US011111390B2

(12) United States Patent
Schilling et al.

(10) Patent No.: US 11,111,390 B2
(45) Date of Patent: Sep. 7, 2021

(54) SURFACE-MODIFIED EFFECT PIGMENT AND NAIL VARNISH COMPOSITION

(71) Applicant: ECKART GmbH, Hartenstein (DE)

(72) Inventors: Christine Schilling, Hartenstein (DE); Ulrich Schmidt, Hartenstein (DE); Christina Pippinger, Hartenstein (DE); Ann-Katrin Gebhard, Hartenstein (DE)

(73) Assignee: ECKART GmbH, Hartenstein (DE)

( * ) Notice: Subject to any disclaimer, the term of this patent is extended or adjusted under 35 U.S.C. 154(b) by 0 days.

(21) Appl. No.: 16/093,717

(22) PCT Filed: Apr. 13, 2017

(86) PCT No.: PCT/EP2017/058980
§ 371 (c)(1),
(2) Date: Oct. 15, 2018

(87) PCT Pub. No.: WO2017/178610
PCT Pub. Date: Oct. 19, 2017

(65) Prior Publication Data
US 2019/0077963 A1 Mar. 14, 2019

(30) Foreign Application Priority Data
Apr. 15, 2016 (EP) .................................... 16000855

(51) Int. Cl.
| C09C 1/64 | (2006.01) |
| A61K 8/26 | (2006.01) |
| A61Q 3/02 | (2006.01) |
| A61K 8/81 | (2006.01) |
| A61K 8/02 | (2006.01) |
| C09C 1/66 | (2006.01) |
| C09C 1/62 | (2006.01) |
| C09C 1/00 | (2006.01) |
| A61K 8/55 | (2006.01) |
| A61K 8/72 | (2006.01) |

(52) U.S. Cl.
CPC ............ *C09C 1/644* (2013.01); *A61K 8/0254* (2013.01); *A61K 8/26* (2013.01); *A61K 8/55* (2013.01); *A61K 8/72* (2013.01); *A61K 8/8117* (2013.01); *A61Q 3/02* (2013.01); *C09C 1/0015* (2013.01); *C09C 1/627* (2013.01); *C09C 1/642* (2013.01); *C09C 1/648* (2013.01); *C09C 1/66* (2013.01); *A61K 2800/412* (2013.01); *A61K 2800/436* (2013.01); *A61K 2800/612* (2013.01); *A61K 2800/651* (2013.01); *A61K 2800/805* (2013.01); *C01P 2004/20* (2013.01); *C01P 2004/61* (2013.01); *C01P 2006/60* (2013.01); *C09C 2200/102* (2013.01); *C09C 2200/301* (2013.01); *C09C 2220/10* (2013.01)

(58) Field of Classification Search
CPC ............................... A61Q 3/00; A61Q 3/02
See application file for complete search history.

(56) References Cited

U.S. PATENT DOCUMENTS

| 5,964,936 A | 10/1999 | Reisser |
| 6,491,932 B1 | 12/2002 | Ramin et al. |
| 6,541,540 B2 * | 4/2003 | Hashizume ............ C09D 5/032 523/205 |
| 6,565,835 B1 | 5/2003 | Socci et al. |
| 6,645,286 B2 | 11/2003 | Ostertag et al. |
| 7,172,812 B2 | 2/2007 | Greiwe et al. |
| 7,828,890 B2 | 11/2010 | Henglein et al. |
| 8,163,079 B2 | 4/2012 | Proelss et al. |
| 8,383,532 B2 | 2/2013 | Fujiwara et al. |
| 8,715,407 B2 | 5/2014 | Schumacher et al. |
| 8,728,226 B2 | 5/2014 | Schumacher et al. |
| 8,728,227 B2 | 5/2014 | Schumacher et al. |
| 8,728,228 B2 | 5/2014 | Schumacher et al. |
| 8,864,899 B2 | 10/2014 | Geissler et al. |
| 9,175,166 B2 | 11/2015 | Geissler et al. |
| 9,237,994 B2 | 1/2016 | Fujiwara et al. |
| 2001/0007696 A1 * | 7/2001 | Kaupp ..................... C08K 9/02 427/216 |
| 2006/0047018 A1 | 3/2006 | Li et al. |
| 2007/0032574 A1 * | 2/2007 | Kaupp ................... C09D 5/028 523/200 |
| 2007/0199478 A1 | 8/2007 | Schlegl et al. |
| 2008/0131383 A1 | 6/2008 | Kruger et al. |
| 2008/0314284 A1 | 12/2008 | Li et al. |
| 2009/0047228 A1 | 2/2009 | Guerchet et al. |
| 2009/0126316 A1 | 5/2009 | Ilekti et al. |
| 2010/0047199 A1 | 2/2010 | Trummer et al. |

(Continued)

FOREIGN PATENT DOCUMENTS

| CN | 1673284 A | 9/2005 |
| CN | 102718229 A | 10/2012 |

(Continued)

OTHER PUBLICATIONS

International Search Report and Written Opinion for International Application No. PCT/EP2017/058980 dated Jun. 21, 2017 (20 pages).

*Primary Examiner* — Gina C Justice
(74) *Attorney, Agent, or Firm* — Fitch, Even, Tabin & Flannery LLP

(57) ABSTRACT

The invention relates to a surface-modified effect pigment comprising particular additives and to the production thereof. The present invention further provides a nail varnish composition comprising a) at least one effect pigment that has been surface-modified with a starting material (additive), where the effect pigment comprises a substrate in platelet form and optionally at least one coating applied to the substrate, b) at least one hydrocarbon resin as binder, and c) at least one solvent or solvent mixture, where the starting material (additive) for surface modification of the effect pigment is at least one compound taken from the group consisting of phosphoric ester-containing, phosphonic ester-containing, phosphonic acid-containing, fatty acid-containing and/or silane-containing compounds or mixtures thereof.

18 Claims, No Drawings

(56) References Cited

U.S. PATENT DOCUMENTS

| | | |
|---|---|---|
| 2010/0269733 A1 | 10/2010 | Kremitzl |
| 2010/0297045 A1 | 11/2010 | Kaupp et al. |
| 2011/0083582 A1 | 4/2011 | Wagner et al. |
| 2011/0160389 A1 | 6/2011 | Bubat et al. |
| 2014/0251184 A1 | 9/2014 | McGuire et al. |
| 2015/0247040 A1* | 9/2015 | Henglein ............ C09D 7/70 106/483 |

FOREIGN PATENT DOCUMENTS

| | | |
|---|---|---|
| DE | 19820112 A1 | 11/1999 |
| DE | 102005036333 A1 | 2/2007 |
| DE | 102007034928 A1 | 1/2009 |
| EP | 289240 B1 | 4/1992 |
| EP | 0723997 A1 | 7/1996 |
| EP | 1082952 A1 | 3/2001 |
| EP | 1251152 A1 | 10/2002 |
| EP | 1299066 A2 | 4/2003 |
| EP | 1462085 A1 | 9/2004 |
| EP | 1746913 A2 | 1/2007 |
| EP | 1792598 A1 | 6/2007 |
| EP | 1796794 A1 | 6/2007 |
| EP | 1812518 A2 | 8/2007 |
| EP | 1980594 B1 | 6/2009 |
| EP | 1829833 B1 | 1/2010 |
| EP | 2217664 A1 | 8/2010 |
| EP | 2227508 A1 | 9/2010 |
| EP | 2248514 A2 | 11/2010 |
| EP | 2318463 A1 | 5/2011 |
| EP | 2346949 A1 | 7/2011 |
| EP | 2346950 A1 | 7/2011 |
| EP | 2356181 A1 | 8/2011 |
| EP | 2367889 A1 | 9/2011 |
| EP | 2042474 B1 | 3/2013 |
| EP | 2576702 A1 | 4/2013 |
| FR | 2939678 A1 * | 6/2010 ............... A61K 8/34 |
| JP | 0374472 A | 3/1991 |
| JP | H09227340 A | 9/1997 |
| JP | H11130633 A | 5/1999 |
| JP | 2002220323 A | 8/2002 |
| JP | 2004189654 A | 7/2004 |
| JP | 2005264144 A | 9/2005 |
| JP | 2006176456 A | 7/2006 |
| JP | 2006199920 A | 8/2006 |
| JP | 2009102300 A | 5/2009 |
| JP | 2011001320 A | 1/2011 |
| JP | 2012081236 A | 4/2012 |
| JP | 2012241062 A | 12/2012 |
| WO | 9638505 A1 | 12/1996 |
| WO | 2004087816 A2 | 10/2004 |
| WO | 2005049739 A2 | 6/2005 |
| WO | 2007148758 A1 | 12/2007 |
| WO | 2008077612 A2 | 7/2008 |
| WO | 2009152941 A2 | 12/2009 |
| WO | 2010024283 A1 | 3/2010 |
| WO | 2010086165 A1 | 8/2010 |
| WO | WO-2015002620 A1 * | 1/2015 |

* cited by examiner

SURFACE-MODIFIED EFFECT PIGMENT AND NAIL VARNISH COMPOSITION

The present invention relates to a surface-modified effect pigment and to a process for production thereof and to nail varnish compositions comprising said surface-modified effect pigment.

EP 1 812 518 A2 discloses pearlescent pigments provided with at least one phosphorus compound on the surface. The pearlescent pigments are especially suitable for use in powder coatings.

EP 2 227 508 A1 describes metal effect pigments coated with at least one metal oxide layer, wherein the surface of the metal oxide layer includes at least one fluoroalkyl- and/or fluoroaryl-containing surface modifier or covalently bonded polysiloxane. The metal effect pigments are especially employed in powder coatings.

EP 2 318 463 A1 discloses metal effect pigments coated with at least one metal oxide layer, wherein the surface of the metal oxide layer includes covalently bonded polysiloxane. The metal effect pigments are especially suitable for use in powder coatings.

EP 2 576 702 A1 relates to the use of surface-modified effect pigments especially in powder coatings. The effect pigment surface here has been surface-modified with at least one compound containing epoxy groups.

EP 1 462 085 A1 discloses a nail varnish composition with a mirror effect which comprises particles having metallic luster in a proportion of ≥2% by weight, based on the total weight of the nail varnish composition. EP 1 462 085 A1 does not disclose any surface-modified effect pigments.

EP 1 299 066 A2 describes a nail varnish comprising aluminum platelets and having a mirror-like appearance. According to EP 1 299 066 A2, the nail varnish has to comprise nitrocellulose having a molecular weight of >56000 as film former for a mirror-like effect to be achievable on a fingernail. Nevertheless, the mirror effects achievable thereby are limited and in need of improvement.

EP 1 746 913 A2 discloses a flexible article comprising at least one bonding layer for fixing of the article on a fingernail, at least one organic film and at least one component responsible for an optical effect, for example. The latter may serve, for example, to impart a mirror effect to the flexible article.

EP 1 792 598 A1 describes a nail varnish having specular gloss, which comprises colloidal precious metal particles having an average particle size of 10 to 100 nm in a proportion of 5% to 50% by weight, based on the total weight of the nail varnish.

EP 1 796 794 A1 discloses a cosmetic composition comprising a PVD aluminum pigment at a pigmentation level of 0.05% to 5.0% by weight, based on the total weight of the cosmetic composition, and at least one leafing additive. Leafing additives used are long-chain phosphoric esters or a mixture of multiple long-chain phosphoric esters. However, the leafing effect is not fully manifested in most nail varnishes.

EP 1 082 952 A1 discloses a cosmetic composition, for example a nail varnish, comprising metal-coated glass particles.

JP 2012081236 A discloses the securing of a mirror on a fingernail.

EP 2 248 514 A2 describes nitrocellulose-free nail varnish compositions comprising at least one styrene/maleic anhydride copolymer as high-gloss film former, at least one epoxy resin as co-film former, at least one reactive component and at least one solvent. The nitrocellulose-free nail varnish composition is said to have comparable or better adhesion properties than nitrocellulose-containing nail varnish compositions. In EP 2 248 514 A2, no surface-modified effect pigments are used as colorants.

It is an object of the present invention to provide an effect pigment for use in a nail varnish composition which is crucial in determining the visual appearance of the nail varnish composition after application and drying. In the case of high-quality metal effect pigments, specular gloss and preferably exceptional specular gloss is to be enabled.

More particularly, it is a further object of the present invention to provide a nail varnish composition that enables a good leafing effect of surface-modified effect pigments.

The object underlying the invention is achieved by the provision of a surface-modified effect pigment comprising a metallic substrate in platelet form that has optionally been coated with at least one metal oxide, metal hydroxide and/or metal oxide hydrate or a nonmetallic substrate in platelet form that has optionally been coated with at least one metal oxide, metal hydroxide and/or metal oxide hydrate, wherein a) the metallic substrate in platelet form is produced by wet grinding and has an $h_{50}$ from a range from 20 nm to less than 100 nm and the starting material (additive) used for surface modification is
  i) phosphoric acid cetyl ester or cetylphosphoric acid from a range from 2% by weight to less than 40% by weight or
  ii) phosphoric acid stearyl ester or stearyl phosphate from a range from 5% by weight to less than 20% by weight or
  iii) phosphonic acids of the formula R—P(O)(OH)$_2$ with R=linear alkyl moiety having a carbon chain from a range from $C_8$ to $C_{14}$, in a total amount preferably from a range from 4% by weight to 45% by weight, based in each case on the total weight of the optionally coated metallic substrate in platelet form, or b) the metallic substrate in platelet form is produced by PVD methods and has an average thickness $h_{50}$ from a range from 13 nm to 60 nm and the starting material (additive) used for surface modification is
  i) phosphoric acid cetyl ester or cetylphosphoric acid from a range from 10% by weight to 50% by weight or
  ii) phosphoric acid stearyl ester or stearyl phosphate from a range from 13% by weight to 50% by weight or
  iii) phosphonic acids of the formula R—P(O)(OH)$_2$ with R=linear alkyl moiety having a carbon chain from a range from $C_8$ to $C_{14}$, in a total amount from a range from 5% by weight to 50% by weight, based in each case on the total weight of the optionally coated metallic substrate in platelet form, or c) the nonmetallic substrate in platelet form has a $D_{50}$ from a range from 2 μm to 360 μm and the starting material (additive) used for surface modification is
  i) phosphoric acid cetyl ester or cetylphosphoric acid from a range from 5% by weight to 30% by weight or
  ii) phosphoric acid stearyl ester or stearyl phosphate from a range from 2% by weight to 25% by weight, based in each case on the total weight of the optionally coated nonmetallic substrate in platelet form, or d) the nonmetallic substrate is a glass platelet that has been coated with metallic silver and has a $D_{50}$ from a range from 2 μm to 360 μm and an average thickness $h_{50,glass}$ of the glass platelet within a range from 70 nm to 530 nm and an average thickness of the metallic silver coating within a range from 9 nm to 27 nm and the starting material (additive) used for surface modification is
  i) phosphoric acid cetyl ester or cetylphosphoric acid from a range from 3% by weight to less than 40% by weight or
  ii) phosphoric acid stearyl ester or stearyl phosphate from a range from 5% by weight to less than 30% by weight or
  iii) phosphonic acids R—P(O)(OH)$_2$ with R=linear alkyl moiety having a carbon chain from a range from $C_8$ to $C_{14}$, in a proportion from a range from 15% by weight to 43% by weight, based in each case on the total weight of the silver-coated glass platelet.

The object of the invention is additionally achieved by a process for producing the surface-modified effect pigment as claimed in claim 3, wherein the process comprises the following steps:
  i. suspending the metallic substrate in platelet form that has optionally been coated with at least one metal oxide, metal hydroxide and/or metal oxide hydrate or the nonmetallic substrate in platelet form that has optionally been coated with at least one metal oxide, metal hydroxide and/or metal oxide hydrate in at least one solvent,
  ii. adding the phosphoric acid cetyl ester or the phosphoric acid stearyl ester or the phosphonic acid at optionally elevated temperature to the suspension from step i. and stirring the suspension then obtained,
  iii. filtering, optionally drying, the surface-modified effect pigment obtained in step ii.

The object of the underlying invention is also achieved by the provision of a nail varnish composition comprising
  a) at least one effect pigment surface-modified with a starting material (additive), where the effect pigment comprises a substrate in platelet form and optionally comprises at least one coating applied to the substrate,
  b) at least one hydrocarbon resin and
  c) at least one solvent or solvent mixture,
wherein the starting material (additive) used for surface modification of the effect pigment is at least one compound from the group consisting of phosphoric ester-containing, phosphonic ester-containing, phosphonic acid-containing, fatty acid-containing and/or silane-containing compounds or mixtures thereof.

Preferred developments of the nail varnish composition are specified in claims 5 to 15.

The object is also achieved by provision of a process for producing the nail varnish composition of the invention as claimed in claim 16.

The object of the underlying invention is also achieved by the use of a surface-modified effect pigment as claimed in claim 1 or 2 in nail varnishes.

The effect pigments surface-modified in accordance with the invention as claimed in claim 1 may comprise a metallic substrate in platelet form that is optionally coated with at least one metal oxide, metal hydroxide and/or metal oxide hydrate or a nonmetallic substrate in platelet form that is optionally coated with at least one metal oxide, metal hydroxide and/or metal oxide hydrate.

The metallic substrates in platelet form may be produced via conventional wet or dry grinding or via PVD methods.

The metallic substrates in platelet form may be selected from the group consisting of aluminum platelets, copper platelets, zinc platelets, iron platelets, titanium platelets, stainless steel platelets, silver platelets, alloys and mixtures of the aforementioned metals. Preferably, the metallic substrates in platelet form are selected from the group consisting of aluminum platelets, copper platelets, zinc platelets, iron platelets, stainless steel platelets, alloys and mixtures of the above-listed metals. The aforementioned metallic substrates in platelet form may also have one or more layers of or comprising at least one metal oxide, metal hydroxide and/or metal oxide hydrate of high and/or low refractive index and may optionally have been dried and/or optionally calcined. For instance, the metallic substrates in platelet form used may thus also be commercially available coated metal effect pigments. In a preferred embodiment, the metallic substrates in platelet form to be used in accordance with the invention have not been coated.

More preferably, the metallic substrates in platelet form are selected from the group consisting of aluminum platelets, copper platelets, zinc platelets, iron platelets, alloys and mixtures of the above-listed metals. Most preferably, the metallic substrates in platelet form are selected from the group consisting of aluminum platelets, copper platelets, zinc platelets, alloys and mixtures of the above-listed metals. Particularly preferably, the metallic substrates in platelet form used are aluminum platelets.

Additionally preferred are aluminum platelets that are produced by PVD methods.

In a preferred embodiment, the metallic substrates in platelet form are PVD pigments, particularly aluminum PVD pigments.

These preferably have an average thickness $h_{50}$ in a range from 13 nm to 80 nm, further preferably from a range from 13 nm to 60 nm and more preferably in a range from 20 nm to 40 nm.

Below 13 nm, the metallic PVD pigments, especially aluminum pigments, become too dark and too transparent.

Above 80 nm, there is a considerable decline in the optical properties and the hiding power, and a specular gloss is achievable only with difficulty.

If metal effect pigments are used in cosmetic formulations, they have to meet certain purity demands, for example the EU Cosmetic Regulation 1223/2009 or FDA 21CFR part 73.

If, for example, aluminum platelets are used as metallic substrate in platelet form, these preferably have an aluminum content of ≥97% by weight, further preferably of ≥98% by weight, more preferably of ≥99% by weight and most preferably of ≥99.7% by weight, based in each case on the total weight of the aluminum platelet. In a preferred embodiment, the aluminum platelets also have a mercury content of preferably ≤1 ppm, an arsenic content of preferably ≤2 ppm, a lead content of preferably ≤10 ppm, a cadmium content of preferably ≤1 ppm, a barium content of preferably ≤10 ppm, a chromium content of preferably ≤20 ppm, a nickel content of preferably ≤20 ppm, a copper content of preferably ≤20 ppm, a cobalt content of preferably ≤20 ppm, an antimony content of preferably ≤2 ppm, a selenium content of preferably ≤10 ppm and a zinc content of preferably ≤20 ppm.

If copper platelets are used as metallic substrate in platelet form, these preferably have a copper content of ≥95% by weight, further preferably of ≥96% by weight, more preferably of ≥97% by weight and most preferably of ≥98% by weight, based in each case on the total weight of the copper platelet. In a preferred embodiment, the copper platelets also have a mercury content preferably of ≤1 ppm, an arsenic content preferably of ≤3 ppm, a lead content preferably of ≤20 ppm, a cadmium content preferably of ≤15 ppm, a barium content preferably of ≤10 ppm, a chromium content preferably of ≤20 ppm, a nickel content preferably of ≤20 ppm, a cobalt content preferably of ≤20 ppm, an antimony content preferably of ≤2 ppm and a selenium content preferably of ≤10 ppm.

If gold bronze platelets are used as metallic substrate in platelet form, these preferably have a copper content from a range from 70% by weight to 95% by weight, a zinc content from a range from <5% by weight to <30% by weight, an aluminum content from a range from 0.01% by weight to ≤1.5% by weight, a tin content from a range from 0.001% by weight to ≤0.5% by weight, based in each case on the total weight of the gold bronze platelets. In a preferred embodiment, the gold bronze platelets also have a mercury content preferably of ≤1 ppm, an arsenic content preferably of ≤3 ppm, a lead content preferably of ≤20 ppm, a cadmium content preferably of ≤15 ppm, a barium content preferably of ≤10 ppm, a chromium content preferably of ≤20 ppm, a nickel content preferably of ≤20 ppm, a cobalt content preferably of ≤20 ppm, an antimony content preferably of ≤2 ppm and a selenium content preferably of ≤10 ppm.

If iron platelets are used as metallic substrate in platelet form, these are preferably produced from reductively treated carbonyl iron powder according to the main claim of EP 1 251 152 A1.

In a further embodiment, the aluminum or aluminum alloy platelets usable as metallic substrate in platelet form are wet-chemically oxidized according to the main claim of WO 96/38505 A1 and optionally have a metal chalcogenide layer of high refractive index according to the main claim of WO 2005/049739 A2.

In a further embodiment, the surface-modified effect pigments to be used in the nail varnish composition of the invention comprise commercially available leafing aluminum effect pigments, for example Eternabrite Premier 251, Eternabrite Premier 255 or Eternabrite Premier 351, each from Silberline.

In a preferred embodiment, the surface-modified effect pigments for use in the nail varnish composition of the invention comprise, as metallic substrate in platelet form, aluminum platelets produced by PVD methods or metal effect pigments according to the main claim of WO 2010/086165 A1, for example METALURE A41010 AE, METALURE A41506 EN, METALURE A 41510 EN, METALURE A31017 AE, METALURE A31010 BG, METALURE A31010 AE, METALURE A21010 AE, METALURE L55350AE, METALURE L63418, METALURE L 55700, METALURE A 61010 BG, METALURE A61010 AE, METALURE A61006 AE, METALURE A61006 BG, METALURE A41010 BG or METALURE L71011AE, all from ECKART GmbH.

The average thickness $h_{50}$ of the metallic substrates in platelet form that are optionally to be coated is preferably within a range from 10 nm to 2000 nm, further preferably within a range from 13 nm to 1500 nm, more preferably within a range from 15 nm to 900 nm and most preferably within a range from 18 nm to 600 nm. The average thickness $h_{50}$ is understood in accordance with the invention to mean the average value of the cumulative distribution curve of the thickness distribution unless stated otherwise.

The determination of $h_{50}$ was preferably effected by the method described in WO 2004/087816 A2 (pages 24 and 25) by means of SEM.

The $h_{50}$ of the cumulative frequency distribution of the thickness distribution function as preferably obtained by counting in the SEM states that 50% of the surface-modified effect pigments measured have a thickness less than or equal to the particular value reported.

In further preferred embodiments, metallic substrates in platelet form used are wet-ground aluminum platelets having a span of the thickness distribution $\Delta h = (h_{90} - h_{10})/h_{50}$ from a range from 30% to 140% and preferably from a range from 30% to 70% and most preferably from a range from 30% to 50%. The production of metal effect pigments of this kind is described in WO 2004/087816 A2 or WO 2008/077612 A2, which are hereby incorporated by reference.

In a further embodiment, metallic substrates in platelet form used are copper platelets or gold bronze platelets having a thickness distribution characterized by an $h_{50}$ of 10 to 50 nm, and an $h_{90}$ of 20 to 70 nm. The production of metallic effect pigments of this kind can be found in WO 2009/152941 A2.

In a further embodiment, the relative standard deviation of the thickness distribution of the metallic substrates in platelet form is 11% to 98%, preferably 22% to 78%, more preferably 28% to 68% and most preferably 34% to 64%. The relative standard deviation in [%] is the quotient of calculated standard deviation of the thickness distribution and average thickness $h_{50}$.

The surface-modified effect pigments of the invention, based on metallic, uncoated substrates in platelet form, to be used with preference in a nail varnish composition may optionally have at least one layer composed of or comprising at least one metal oxide, metal hydroxide and/or metal oxide hydrate, where the metal ion is selected from the group of the metals consisting of Al, Si, Sn, Zn, Ti and Fe, preferably selected from the group of the metals consisting of Al and Si. Above-listed metal oxides, metal hydroxides and/or metal oxide hydrates may take the form of (i) separate layers, (ii) mixed metal oxide, mixed metal hydroxide and/or mixed metal oxide hydrate or (iii) be in separate layers on the metallic substrate in platelet form.

The surface-modified effect pigments of the invention, based on metallic substrates in platelet form, to be used preferably in a nail varnish composition, may have any average particle size $D_{50}$. The $D_{50}$ values of the surface-modified effect pigments of the invention, based on metallic substrates in platelet form, to be used preferably in a nail varnish composition, are preferably within a range from 2 µm to 150 µm, further preferably within a range from 2.5 µm to 170 µm, further preferably within a range from 3 µm to 140 µm, more preferably within a range from 3.5 µm to 90 µm and most preferably within a range from 3.8 µm to 56 µm. Exceptionally preferably, the surface-modified effect pigments of the invention, based on metallic substrates in platelet form, to be used with preference in a nail varnish composition have a $D_{50}$ from a range from 2.5 µm to 14 µm or from a range from 15 µm to 35 µm. Below 2 µm there is a distinct decrease in gloss values, and above 150 µm no uniformly continuous metallic surface is obtained.

Preferably, the metallic substrates in platelet form that have been produced by wet grinding and have an average thickness $h_{50}$ below 100 nm have a $D_{50}$ from a range from 8 µm to 25 µm.

The $D_{10}$ values of the surface-modified effect pigments of the invention, based on metallic substrates in platelet form, to be used with preference in a nail varnish composition are preferably within a range from 1 µm to 60 µm, further preferably within a range from 2 µm to 40 µm, more preferably within a range from 4 µm to 31 µm and most preferably within a range from 5 µm to 19 µm. Below 1 µm there is a distinct decrease in gloss values, and above 60 µm no uniformly continuous metallic surface is obtained.

The $D_{90}$ values of the surface-modified effect pigments of the invention, based on metallic substrates in platelet form, to be used with preference in a nail varnish composition are preferably within a range from 10 µm to 600 µm, further preferably within a range from 30 µm to 200 µm, more preferably within a range from 40 µm to 150 µm and most preferably within a range from 45 µm to 120 µm. Below 10 µm there is a distinct decrease in gloss values, and above 600 µm no uniformly continuous metallic surface is obtained.

In one embodiment, the surface-modified effect pigments of the invention, based on metallic substrates in platelet form, to be used preferably in a nail varnish composition, have a span ΔD, defined as $$\Delta D = \frac{D_{90} - D_{10}}{D_{50}},$$

from a range from 0.7 to 2.5, preferably from a range from 0.8 to 2.2, further preferably from a range from 0.9 to 1.9, more preferably from a range from 0.9 to 1.8 and most preferably from a range from 1 to 1.7.

In a further embodiment, the surface-modified effect pigments of the invention, based on metallic substrates in platelet form, to be used with preference in a nail varnish composition have an aspect ratio, defined as the quotient of $D_{50}$ and average thickness, preferably from a range from 10 to 2000, further preferably from a range from 30 to 1200, more preferably from a range from 100 to 1100 and most preferably from a range from 200 to 1000. Below the lower limits the optical properties of the metallic effect pigments are still insufficient for achievement of specular gloss, and above 2000 the metallic effect pigments are producible only with great difficulty.

In a further embodiment, the surface-modified effect pigments of the invention, based on metallic substrates in platelet form, to be used preferably in a nail varnish composition, preferably have an average total thickness $h_{50}$ from a range from 20 nm to 4000 nm, further preferably from a range from 30 nm to 3000 nm, more preferably from a range from 70 nm to 2000 nm and most preferably from a range from 230 nm to 1300 nm. Average total thickness is understood to mean the complete average thickness of the surface-modified effect pigment, i.e. metallic substrate in platelet form plus optional coating plus surface modification.

In a preferred embodiment, the surface-modified effect pigments of the invention that are to be used preferably in a nail varnish composition, comprise as metallic substrate in platelet form, metal platelets produced by a PVD method having a $D_{50}$ from a range from 2.5 µm to 90 µm, further preferably from a range from 8 µm to 25 µm, and an average thickness from a range from 13 nm to 60 nm. In this embodiment, the aluminum platelets are preferably not coated. The oxide layer naturally present on aluminum platelets is not regarded here as an applied coating.

Surprisingly, it is also possible to achieve specular gloss effects with very small PVD pigments. These pigments can be produced, for example, by further grinding standard PVD pigments or comminuting them by the action of ultrasound.

More preferably, these metal platelets are aluminum platelets.

More preferably, these aluminum PVD pigments have a $D_{50}$ within in a range from 6 µm to 18 µm and an average thickness within a range from 14 nm to 40 nm. Most preferred are aluminum PVD pigments having a $D_{50}$ within a range from 7 µm to 16 µm and an average thickness within a range from 15 nm to 35 nm.

In further embodiments, wet-ground metal platelets and especially aluminum platelets having a similar average thickness to PVD pigments are used.

Thus, preference is given to wet-ground metal platelets and especially aluminum platelets having an average thickness $h_{50}$ from a range from 20 to less than 100 nm and most preferably an average thickness $h_{50}$ from a range from 25 to 60 nm.

Metal effect pigments of this kind can also be used to achieve specular gloss effects, although metal pigments produced by PVD methods generally give even better results.

The nonmetallic substrates in platelet form may be selected from the group consisting of natural mica platelets, synthetic mica platelets, glass platelets, $SiO_2$ platelets, $Al_2O_3$ platelets, kaolin platelets, talc platelets and bismuth oxychloride platelets. The surface-modified effect pigments of the invention that are to be used with preference in a nail varnish composition or the surface-modified effect pigments as claimed in claim 1 may also be based on mixtures of the above-specified nonmetallic substrates in platelet form. The aforementioned nonmetallic substrates in platelet form may also have one or more layers composed of or comprising at least one metal oxide, metal hydroxide and/or metal oxide hydrate of high and/or low refractive index and may have been calcined. For instance, substrates used may thus also be pearlescent pigments or interference pigments.

Preferably, the nonmetallic substrates in platelet form are selected from the group consisting of natural mica platelets, synthetic mica platelets, glass platelets, $SiO_2$ platelets, $Al_2O_3$ platelets and mixtures thereof. More preferably, the nonmetallic substrates in platelet form are selected from the group consisting of natural mica platelets, synthetic mica platelets, glass platelets and mixtures thereof. Most preferred nonmetallic substrates in platelet form are synthetic mica platelets and/or glass platelets. Glass platelets in particular are preferred as nonmetallic substrate in platelet form.

The glass platelets usable as nonmetallic substrate in platelet form may, with regard to their composition, consist of silicate glass, such as soda-lime glass, lead crystal glass, E glass, A glass, C glass, ECR glass, Duran glass, window glass, laboratory glass, aluminosilicate glass or borosilicate glass. The glass platelets preferably have a composition corresponding to the teaching, especially corresponding to the main claim, of EP 1 980 594 B1, more preferably corresponding to the teaching, especially corresponding to the respective main claims, of EP 1 829 833 B1 or of EP 2 042 474 B1. The glass platelets usable as nonmetallic substrate in platelet form are preferably produced by the process described in EP 289 240 B1.

In one embodiment, the glass platelets can be specifically colored through the addition of at least one inorganic colorant in the production thereof. Suitable colorants are those that do not break down at the respective melting temperature of the glass composition. The total proportion of colorant here is preferably within a range from 0.1% by weight to 20% by weight, more preferably within a range from 0.2% by weight to 15% by weight and most preferably within a range from 0.5% by weight to 10% by weight, based in each case on the total weight of the glass composition. Suitable colorants are especially elemental precious metals, such as Au, Pd or Pt, the cations or complex anions of the elements Cu, Cr, Mn, Fe, Ti and/or Co, and mixtures of the above-listed colorants.

In a further embodiment, the refractive index of the glass platelets usable as nonmetallic substrate in platelet form is within a range from 1.45 to 1.80, preferably within a range from 1.50 to 1.70.

In a further embodiment, the nonmetallic substrates in platelet form, especially glass platelets, may have been coated with a layer comprising or consisting of silicon oxide, silicon hydroxide, silicon oxide hydrate. For example, the aforementioned coating, in the case of use of glass platelets, can protect the glass surface from chemical alteration, such as swelling, leaching of glass constituents or dissolution in aggressive acidic coating solutions.

The synthetic mica platelets usable as nonmetallic substrate in platelet form may have a composition according to the main claim of CN 102718229 A or according to the main claim of US 2014/0251184 A1. They may additionally be produced according to the details in EP 0 723 997 A1, page 3 to page 4.

The synthetic mica platelets usable as nonmetallic substrate in platelet form are preferably fluorphlogopite platelets of the formula $KMg_3AlSi_3O_{10}F_2$, $KMg_2½(Si_4O_{10})F_2$ or $NaMg_2½(Si_4O_{10})F_2$, especially fluorphlogopite platelets of the formula $KMg_3AlSi_3O_{10}F_2$, which, according to x-ray fluorescence analysis (XRF), preferably have the constituents specified in table 1 in the form of the respective metal oxide within the ranges listed therein.

TABLE 1

Preferred compositions of synthetic mica platelets according to XRF analysis
Composition of synthetic mica platelets, figures in % by weight, based in each case on the total weight of the synthetic mica platelets

| | |
|---|---|
| $SiO_2$ | 38 to 46 |
| $Al_2O_3$ | 10 to 14 |
| $K_2O$ | 9 to 13 |
| $Fe_2O_3$ | 0.01 to 0.25 |
| MgO | 26 to 34 |
| MnO | 0 to 0.05 |
| $Na_2O$ | 0 to 13 |

The average thickness $h_{50}$ of the nonmetallic substrates in platelet form that are optionally to be coated is preferably within a range from 50 nm to 5000 nm, more preferably within a range from 60 nm to 3000 nm and most preferably within a range from 70 nm to 2000 nm.

In one embodiment, the average thickness $h_{50,glass}$ for glass platelets as nonmetallic substrate in platelet form which is optionally to be coated is within a range from 750 nm to 1500 nm, preferably within a range from 850 nm to 1400 nm and more preferably within a range from 900 nm to 1300 nm. Thinner nonmetallic substrates in platelet form lead to a lower total thickness of the surface-modified effect pigments of the invention that are to be used with preference in a nail varnish composition and optionally to be coated, or of the surface-modified effect pigments as claimed in claim 1. Thus, likewise preferred as nonmetallic substrate in platelet form are glass platelets having an average thickness $h_{50,glass}$ within a range from 50 nm to 700 nm, further preferably within a range from 101 nm to 600 nm, more preferably within a range from 160 nm to 500 nm and most preferably within a range of 200 nm to 400 nm.

In a further embodiment, the average thickness $h_{50,mica}$ of the natural or synthetic mica platelets as nonmetallic substrate in platelet form which is optionally to be coated is preferably within a range from 80 nm to 1300 nm, further preferably within a range from 90 nm to 1000 nm, more preferably within a range from 99 nm to 800 nm and most preferably within a range from 200 nm to 600 nm.

If nonmetallic substrates in platelet form below an average thickness $h_{50}$ of 50 nm are coated with metal oxides of high refractive index, for example, extremely fracture-sensitive effect pigments are obtained that can break up even on incorporation into the respective application medium, which in turn causes significant lowering of the gloss.

Above an average thickness of the nonmetallic substrate in platelet form of 5000 nm, the effect pigments overall can become too thick. This is associated with poorer specific hiding capacity, meaning that the area covered per unit weight of effect pigment is lower. Moreover, such thick effect pigments have a lower degree of plane-parallel orientation to the substrate in the application medium. Poorer orientation in turn results in reduced gloss. With regard to tactile properties too, excessively thick effect pigments can be disadvantageous overall in any application.

In one embodiment, the relative standard deviation of the thickness distribution of the nonmetallic substrates in platelet form is 15% to 100%, preferably 17% to 70%, more preferably 19% to 61% and most preferably 21% to 41%. The relative standard deviation in [%] is the quotient of calculated standard deviation and average thickness $h_{50}$.

The nonmetallic substrates in platelet form may optionally be coated with at least one metal oxide, metal hydroxide and/or metal oxide hydrate. This optional coating may have at least one layer of high refractive index and/or at least one layer of low refractive index.

A layer of high refractive index is understood to mean a layer having a refractive index of n≥1.8, preferably of n≥2.0 and more preferably of n≥2.2. A layer of low refractive index is understood to mean a layer having a refractive index of n<1.8 and preferably of n<1.6. For classification into layers of high and low refractive index, refractive indices known from literature are employed.

The optionally present coating may comprise at least one layer of high refractive index composed of or comprising at least one metal oxide, metal hydroxide and/or metal oxide hydrate, where the metal ion is selected from the group of metals consisting of Ti, Fe, Sn, Mn, Zr, Ca, Sr, Ba, Ni, Ag, Zn, Cu, Ce, Cr and Co, preferably selected from the group of metals consisting of Ti, Fe, Sn, Zr, Ag, Zn, Cu, Ce and Cr, and more preferably selected from the group of metals consisting of Ti, Fe and Sn. Above-listed metal oxides, metal hydroxides and/or metal oxide hydrates may take the form of (i) a mixed layer or (ii) a mixed metal oxide, mixed metal hydroxide and/or mixed metal oxide hydrate, preferably of an iron titanate, such as ilmenite, pseudobrookite or pseudorutile, or (iii) be present in separate layers on the nonmetallic substrate in platelet form.

Alternatively or additionally to the aforementioned at least one layer of high refractive index, the coating optionally present may comprise at least one layer of low refractive index composed of or comprising at least one metal oxide, metal hydroxide and/or metal oxide hydrate, where the metal ion is selected from the group of metals consisting of Si, Al and B. If layers of high and low refractive index are present in the coating optionally present, these are preferably present alternately.

In one embodiment, the at least one layer of high refractive index and/or the at least one layer of low refractive index may have been doped, where the doping may comprise metal oxides, metal hydroxides and/or metal oxide hydrates wherein the metal ion is selected from the group of metals consisting of Al, Ce, Zr and Sn, preferably consisting of Al, Zr and Sn. The total proportion of doping is preferably ≤1% by weight, more preferably ≤0.5% by weight and most preferably ≤0.2% by weight, based in each case on the total weight of the surface-modified effect pigments.

In a further embodiment, the coating optionally present may, alternatively or additionally to the layer comprising at least one metal oxide, metal hydroxide and/or metal oxide hydrate, comprise at least one semitransparent metal layer. The metals of the semitransparent metal layer may be selected from the group consisting of Ag, Al, Cr, Ni, Au, Pt, Pd, Cu, Zn and Ti, preferably selected from the group consisting of Ag, Au and Cu. The semitransparent metal layer may of course also comprise alloys or mixtures of the above-listed metals. The average thickness of the semitransparent metal layer is preferably within a range from 1 nm to 30 nm, more preferably within a range from 4 nm to 26 nm and more preferably within a range from 7 nm to 21 nm.

In a preferred embodiment, the nonmetallic substrates in platelet form include at least one of the above-described layers, more preferably at least one layer composed of or comprising metal oxides, metal hydroxides and/or metal oxide hydrates of high refractive index.

In a further embodiment, the surface-modified effect pigments of the invention that are to be used with preference in a nail varnish composition or the surface-modified effect pigments as claimed in claim 1, based in each case on nonmetallic substrates in platelet form, have a span ΔD, defined as $$\Delta D = \frac{D_{90} - D_{10}}{D_{50}},$$

from a range from 0.7 to 2.0, preferably from a range from 0.7 to 1.5, further preferably from a range from 0.8 to 1.3, more preferably from a range from 0.8 to 1.2 and most preferably from a range from 0.85 to 1.1. The advantages of a narrow size classification in relation to color purity and/or gloss of the resulting effect pigments are described, for example, in EP 2 217 664 A1, EP 2 346 950 A1, EP 2 356 181 A1, EP 2 346 949 A1, EP 2 367 889 A1.

The surface-modified effect pigments of the invention, based on nonmetallic substrates in platelet form, to be used preferably in a nail varnish composition, have an average particle size $D_{50}$ from a range from 2 μm to 360 μm. The $D_{50}$ values of the surface-modified effect pigments of the invention, based on nonmetallic substrates in platelet form, to be used with preference in a nail varnish composition are preferably within a range from 3 μm to 350 μm, further preferably within a range from 4 μm to 211 μm, further preferably within a range from 6 μm to 147 μm, more preferably within a range from 7 μm to 99 μm and most preferably within a range from 8 μm to 56 μm. Exceptionally preferably, the surface-modified effect pigments of the invention, based on nonmetallic substrates in platelet form, to be used with preference in a nail varnish composition have a $D_{50}$ value from a range from 3 to 15 μm or from a range from 10 to 35 μm or from a range from 25 to 45 μm or from a range from 30 to 65 μm or from a range from 40 to 140 μm or from a range from 135 to 250 μm.

The $D_{10}$ values of the surface-modified effect pigments of the invention, based on nonmetallic substrates in platelet form, to be used with preference in a nail varnish composition are preferably within a range from 1 to 120 μm. More preferably, the $D_{10}$ values of the surface-modified effect pigments of the invention, based on nonmetallic substrates in platelet form, to be used preferably in a nail varnish composition are within a range from 1 μm to 5 μm or within a range from 5 μm to 25 μm or within a range from 10 μm to 30 μm or within a range from 20 μm to 45 μm or within a range from 25 μm to 65 μm or within a range from 75 to 110 μm.

The $D_{90}$ values of the surface-modified effect pigments of the invention, based on nonmetallic substrates in platelet form, to be used with preference in a nail varnish composition are preferably within a range from 6 to 500 μm. More preferably, the $D_{90}$ values of the surface-modified effect pigments of the invention, based on nonmetallic substrates in platelet form, to be used preferably in a nail varnish composition are within a range from 8 μm to 250 μm or within a range from 10 μm to 150 μm or within a range from 40 μm to 70 μm or within a range from 68 μm to 110 μm or within a range from 120 μm to 180 μm or within a range from 400 μm to 490 μm.

In a particularly preferred embodiment, the surface-modified effect pigments for use in a nail varnish composition comprise, as nonmetallic substrate in platelet form, glass platelets having a $D_{50}$ from a range from 9 μm to 390 μm, an average thickness from a range from 90 nm to 590 nm, preferably from a range from 110 nm to 340 nm, a glass composition according to the main claim of WO 2007/148758 A1 or of WO 2010/024283 A1 and a semitransparent layer composed of or comprising metallic silver.

The average thickness of the metallic or nonmetallic substrate in platelet form that has been coated with a metal oxide, metal hydroxide and/or metal oxide hydrate and the average total thickness of the surface-modified effect pigment is determined using a cured paint film in which the surface-modified effect pigments of the invention that are to be used preferably in a nail varnish composition are aligned essentially plane-parallel to the substrate. For this purpose, a cross section of the cured paint film is examined under a scanning electron microscope (SEM) to determine the thickness of the metallic or nonmetallic substrate in platelet form or the total thickness of the surface-modified effect pigment for at least 100 surface-modified effect pigments and find the statistical average. According to the invention, the term "average" always means the $h_{50}$, unless stated otherwise.

In the case of surface-modified effect pigments of the invention that are to be used with preference in a nail varnish composition and have not been coated with a metal oxide, metal hydroxide and/or a metal oxide hydrate, the average thickness $h_{50}$ is preferably determined by the method described in WO 2004/087816 A2 (pages 24 and 25) by means of SEM.

The $D_{10}$, $D_{50}$ and $D_{90}$ values of the cumulative frequency distribution of the volume-averaged size distribution function as obtained by laser diffraction methods mean that, respectively, 10%, 50% and 90% of the surface-modified effect pigments analyzed have a volume-averaged diameter of less than or equal to the value specified in each case. In this context, the size distribution curve of the surface-modified effect pigments of the invention that are to be used with preference in a nail varnish composition and of the surface-modified effect pigments as claimed in claim 1, based in each case on nonmetallic substrates in platelet form, are determined with the Malvern Mastersizer 2000 instrument according to the manufacturer's instructions. The scattered light signals are evaluated by the Fraunhofer theory, which also includes refraction and absorption characteristics of the particles. The size distribution curve of the surface-modified effect pigments of the invention that are to be used with preference in a nail varnish composition and of the surface-modified effect pigments as claimed in claim 1, based in each case on metallic substrates in platelet form, are ascertained with the Quantachrome Cilas 1064 instrument or the Horiba LA-930 instrument. The scattered light signals are evaluated by the Fraunhofer theory, which also includes refraction and absorption characteristics of the particles.

It has been found that the effect pigments surface-modified in accordance with the invention do not show good results in all nail varnish systems as disclosed, for example, in EP 1796794 B2. Frequently, the leafing effect is lost on application or thereafter, with the associated effect that the optical properties of the effect pigments are not fully manifested.

Therefore, an essential constituent of the present invention is the provision of a nail varnish in which the leafing properties of the surface-modified effect pigments are very well manifested.

The invention is therefore also directed to a nail varnish composition comprising
a) at least one effect pigment surface-modified with a starting material (additive), where the effect pigment is a substrate in platelet form and optionally comprises at least one coating applied to the substrate,
b) at least one hydrocarbon resin and
c) at least one solvent or solvent mixture,
wherein the starting material (additive) used for surface modification of the effect pigment is at least one compound from the group consisting of phosphoric ester-containing, phosphonic ester-containing, phosphonic acid-containing, fatty acid-containing and/or silane-containing compounds or mixtures thereof.

The phosphoric esters and/or phosphoric acids and/or phosphonic esters and/or phosphonic acids usable for surface modification may be phosphoric esters of the general formula $(R-O)_n-P(O)(OR')(OR'')_m$ or phosphonic esters of the general formula $R-P(O)(OR')(OR'')$ where the R, R' and R'' moieties are preferably defined as follows: R=linear and/or branched alkyl moiety having a carbon chain from a range from $C_{10}$ to $C_{20}$ and R'=R''=H, linear and/or branched alkyl moiety having a carbon chain from a range from $C_1$ to $C_6$, preferably $C_1$ to $C_3$, where R' and R'' may be identical or different and where n=1 or 2 and m=n−1 and n+m=2.

In this context, with regard to the number n, it is possible for either pure forms of the monoesters (n=1) or diesters (n=2) or mixtures thereof to be present.

In a particularly preferred embodiment, surface modification of the effect pigments for use in a nail varnish composition of the invention is accomplished using primary phosphoric acids or phosphonic acids with R=linear unsubstituted alkyl moiety having a carbon chain from a range from $C_{12}$ to $C_{18}$, preferably from a range from $C_{14}$ to $C_{18}$ and R'=R''=H. Further preferably in this context, n=1 (monoester).

A preferred phosphonic acid is laurylphosphonic acid and preferred phosphoric acids are cetyl phosphate or stearyl phosphate.

Surface modification can be accomplished using, for example, 2-ethylhexylphosphoric ester (CAS: 12645-31-7), laurylphosphoric ester (CAS: 12751-23-4), cetylphosphoric ester (CAS: 3539-43-3), stearylphosphoric ester (CAS: 39471-52-8) and/or monoethylmono-(9Z)-9-octadecenylphosphoric ester (CAS: 10483-96-2).

Particular preference is given to cetylphosphoric ester, stearylphosphoric ester or laurylphosphoric ester and particular preference is given to cetylphosphoric ester or stearylphosphoric ester and very particular preference is given to cetylphosphoric ester.

The fatty acids usable for surface modification may be fatty acids of the general formula R—COOH where the R moiety is preferably defined as follows:
i. R=linear and/or branched alkyl moiety having a carbon chain from a range from $C_{12}$ to $C_{26}$, preferably from a range from $C_{14}$ to $C_{24}$, further preferably from a range from $C_{16}$ to $C_{22}$ and more preferably from a range from $C_{18}$ to $C_{20}$; or
ii. R=linear and/or branched alkenyl moiety having a carbon chain from a range from $C_{12}$ to $C_{26}$, preferably from a range from $C_{14}$ to $C_{24}$, further preferably from a range from $C_{16}$ to $C_{22}$ and more preferably from a range from $C_{18}$ to $C_{20}$; or
iii. R=linear and/or branched alkynyl moiety having a carbon chain from a range from $C_{12}$ to $C_{26}$, preferably from a range from $C_{14}$ to $C_{24}$, further preferably from a range from $C_{16}$ to $C_{22}$ and more preferably from a range from $C_{18}$ to $C_{20}$.

In a preferred embodiment, surface modification of the effect pigments usable in a nail varnish composition of the invention is accomplished using fatty acids with R=linear unsubstituted alkyl moiety having a carbon chain from a range from $C_{12}$ to $C_{20}$, preferably from a range from $C_{14}$ to $C_{18}$.

The silanes usable for surface modification may be silanes of the general formula $R-Si(OR')_3$ where the R and R' moieties are preferably defined as follows: R=linear and/or branched alkyl moiety having a carbon chain from a range from $C_6$ to $C_{23}$, preferably from a range from $C_7$ to $C_{20}$, more preferably from a range from $C_8$ to $C_{18}$ and R'=linear and/or branched alkyl moiety having a carbon chain from a range from $C_1$ to $C_4$, preferably from a range from $C_1$ to $C_3$ and more preferably from a range from $C_1$ to $C_2$, where the alkyl moiety R in further embodiments may comprise at least one substituent selected from the group consisting of —OH, —OCH$_3$, —OC$_2$H$_5$, —NH$_2$, linear and/or branched alkyl moiety having a carbon chain from a range from $C_1$ to $C_6$.

For production of the surface-modified effect pigments of the invention for use with preference in a nail varnish composition, the starting material (additive) for surface modification is preferably used in an amount from a range from 1.5% by weight to 50% by weight, more preferably from a range from 3.2% by weight to 40% by weight and most preferably from a range from 4.8% by weight to 23% by weight, based in each case on the total weight of the effect pigment used.

Since the amounts of the additive specified here are based on the starting material, the actual amount of additive in the ready-coated effect pigment may be smaller since, for example, in the case of an amount of 50% by weight, not all the additive can be absorbed onto the pigment surface. Accordingly, it is also possible for smaller amounts of the leafing additives to be found in the applications comprising the pigments, especially in nail varnishes.

The effect of the quite high amounts of additive in the starting material is very high and dense coating of the effect pigment surface with the additive.

In a particularly preferred embodiment, the starting material (additive) used for surface modification of effect pigments based on metallic substrates in platelet form that have been produced by wet grinding and have an average substrate thickness $h_{50}$ from a range from 20 nm to 100 nm is at least one phosphonic acid of the formula $R-P(O)(OH)_2$ with R=linear alkyl moiety having a carbon chain from a range from $C_8$ to $C_{14}$, in a total amount preferably from a range from 4% by weight to 45% by weight, further preferably from a range from 5% by weight to 43% by weight, more preferably from a range from 6% by weight to 42% by weight and most preferably from a range from 9% by weight to 41% by weight, based in each case on the total weight of the effect pigment used.

In a further particularly preferred embodiment of the invention, the starting material (additive) used for surface modification of effect pigments based on metallic substrates in platelet form that have been produced by PVD methods and have an average substrate thickness $h_{50}$ from a range from 13 nm to 60 nm is at least one phosphonic acid of the formula R—P(O)(OH)$_2$ with R=linear alkyl moiety having a carbon chain from a range from $C_8$ to $C_{14}$, in a total amount from a range from 5% by weight to 50% by weight, further preferably from a range from 6% by weight to 48% by weight, more preferably from a range from 7% by weight to 45% by weight and most preferably from a range of 10% by weight to 42% by weight, based in each case on the total weight of the effect pigment used.

Insufficient leafing of the effect pigments takes place below the specified amounts of phosphonic ester. Above the specified amounts of phosphonic ester, it is possible for excessively large amounts of the phosphonic acids to be introduced into the finished nail varnish composition.

In this context, it is particularly preferable that the effect pigments are coated with the phosphonic ester in a separate step before they are introduced into the nail varnish system.

In a further preferred embodiment, the starting material (additive) used for surface modification of effect pigments based on metallic substrates in platelet form that may have been produced by wet grinding or via PVD methods, having an average substrate thickness from a range from 20 nm to 90 nm, is at least one fatty acid in a total amount from a range from preferably 4% by weight to 28% by weight, further preferably from a range from 4% by weight to 25% by weight, more preferably from a range from 6% by weight to 20% by weight and most preferably from a range from 8% by weight to 17% by weight, based in each case on the total weight of the effect pigment used.

In a further preferred embodiment, the starting material (additive) used for surface modification of effect pigments based on metallic substrates in platelet form that may have been produced by wet grinding or via PVD methods, having an average substrate thickness from a range from 20 nm to 90 nm, is at least one silane in a total amount preferably from a range from 5% by weight to 39% by weight, further preferably from a range from 10% by weight to 35% by weight, more preferably from a range from 15% by weight to 32% by weight and most preferably from a range from 18% by weight to 30% by weight, based in each case on the total weight of the effect pigment used.

In very particularly preferred embodiments, at least one phosphoric ester and/or at least one phosphoric acid of the formula $(R—O)_n—P(O)(OR')(OR'')_m$ where each R=linear alkyl moiety having a carbon chain from a range from $C_{14}$ to $C_{18}$, and where R' and R'' are each independently H, $CH_3$, $C_2H_5$ or $C_3H_8$ and where n=1 or 2 and m=n−1 and n+m=2, in a total amount from a range from 14% by weight to 40% by weight, based on the total weight of the effect pigment used, are used as starting material (additive) for surface modification of effect pigments based on metallic substrates in platelet form that have been produced by PVD methods, having an average substrate thickness $h_{50}$ from a range from 15 nm to 40 nm, preferably 20 to 40 nm. Further preferably, in this context, R'=R''=H. In addition, it is particularly preferable that n=1.

In very particularly preferred embodiments, at least one phosphoric ester and/or a phosphoric acid of the formula $(R—O)_n—P(O)(OR')(OR'')_m$ where each R=linear alkyl moiety having a carbon chain from a range from $C_{14}$ to $C_{18}$, and where R' and R'' are independently H, $CH_3$, $C_2H_5$ or $C_3H_8$, and where n=1 or 2 and m=n−1 and n+m=2, in a total amount from a range from 14% by weight to 31% by weight, based on the total weight of the effect pigment used, are used as starting material (additive) for surface modification of effect pigments based on metallic substrates in platelet form that have been produced by wet grinding, having an average substrate thickness from a range from more than 40 nm to 90 nm, preferably from 45 nm to 80 nm. Further preferably, in this context, R'=R''=H. In addition, it is particularly preferable that n=1.

In further-preferred embodiments, at least one fatty acid R—COOH with R=linear alkyl moiety having a carbon chain from a range from $C_{15}$ to $C_{19}$ in a total amount from a range from 11% by weight to 15% by weight, based on the total weight of the effect pigment used, is used as starting material (additive) for surface modification of effect pigments based on metallic substrates in platelet form having an average substrate thickness from a range from 20 nm to 90 nm, and/or at least one silane R—Si(OR')$_3$ with R=linear alkyl moiety having a carbon chain from a range from $C_{14}$ to $C_{20}$ in a total amount from a range from 21% by weight to 29% by weight, based on the total weight of the effect pigment used, is used for surface modification of effect pigments based on metallic substrates in platelet form having an average substrate thickness from a range from 20 nm to 90 nm.

According to the invention, "total amount" is understood to mean the complete amount of starting material (additive), irrespective of whether the starting material is exclusively at least one phosphoric ester or exclusively at least one phosphonic ester or a mixture of at least one phosphoric ester and at least one phosphonic ester or a mixture of different phosphonic acids or a mixture of different fatty acids or a mixture of different silanes.

The surface-modified effect pigments of the invention as claimed in claim 1 may find use in cosmetic formulations, especially in nail varnish compositions. A particular feature of the surface-modified effect pigments as claimed in claim 1 in nail varnish compositions is their excellent leafing characteristics.

Nail Varnish Composition of the Invention:

The invention is further directed to a nail varnish composition that enables and maintains the leafing effect of the effect pigments in an excellent manner.

This nail varnish composition of the invention comprises:
  a) at least one effect pigment surface-modified with a starting material (additive), where the effect pigment comprises a substrate in platelet form and optionally comprises at least one coating applied to the substrate,
  b) at least one hydrocarbon resin as binder and
  c) at least one solvent or solvent mixture,
  wherein the starting material (additive) used for surface modification of the effect pigment is at least one compound from the group consisting of phosphoric ester-containing, phosphonic ester-containing, phosphonic acid-containing, fatty acid-containing and/or silane-containing compounds or mixtures thereof.

The nail varnish composition of the invention comprising at least one surface-modified effect pigment, by contrast with most commercially available nail varnish compositions, preferably does not include any nitrocellulose. The visual appearance of the nail varnish composition of the invention, after application and drying, is determined to a crucial degree by the at least one surface-modified effect pigment.

The nail varnish composition of the invention comprises the at least one surface-modified effect pigment preferably in a proportion from a range from 0.3% by weight to 8.5% by weight, further preferably from a range from 0.5% by weight to 5.0% by weight, more preferably from a range from 0.6% by weight to 3.0% by weight and most preferably from a range from 0.8% by weight to 1.9% by weight, based in each case on the total weight of the nail varnish composition.

In a particularly preferred embodiment, the nail varnish composition of the invention comprises at least one surface-modified, optionally coated aluminum pigment, where the surface-modified aluminum pigment has a $D_{50}$ from a range from 5 µm to 100 µm, preferably from a range from 2 µm to 60 µm, and the average thickness of the aluminum platelet is within a range from 10 nm to 100 nm, preferably within a range from 20 nm to 40 nm. In this embodiment, the starting material (additive) used for surface modification of the optionally coated aluminum pigment is preferably at least one phosphoric ester R—O—P(O)(OR')(OR") with R=linear alkyl moiety having a carbon chain from a range from $C_{14}$ to $C_{18}$, R'=R"=H in a proportion from a range from 10% by weight to 50% by weight, based on the total weight of the effect pigment used. The nail varnish composition of the invention here comprises the above-described surface-modified, optionally coated aluminum pigment preferably in a proportion from a range from 0.6% by weight to 3.0% by weight, more preferably from a range from 0.8% by weight to 1.9% by weight, based in each case on the total weight of the nail varnish composition.

Below the amounts of the specific substances to be used as starting material (additive) for surface modification that are specified for the effect pigments surface-modified in accordance with the invention as claimed in claim 1 or the various above-described effect pigment/additive combinations for the respective different types of effect pigment, insufficient leafing of the effect pigments takes place. Above the amounts of the additives specified in each case, excessively large amounts of the additives may possibly be introduced into the finished nail varnish composition.

It is particularly preferable here that the effect pigments are coated with the additive in a separate step before they are introduced into the nail varnish system.

A preferred process for producing the surface-modified effect pigments of the invention therefore comprises the following steps:
  i. suspending the metallic substrate in platelet form that has optionally been coated with at least one metal oxide, metal hydroxide and/or metal oxide hydrate or the nonmetallic substrate in platelet form that has optionally been coated with at least one metal oxide, metal hydroxide and/or metal oxide hydrate in at least one solvent,
  ii. adding the phosphoric acid cetyl ester or the phosphoric acid stearyl ester at optionally elevated temperature to the suspension from step i. and stirring the suspension then obtained,
  iii. filtering, optionally drying, the surface-modified effect pigment obtained in step II.

The solvent used is preferably a solvent compatible with the nail varnish of the invention. Particular preference is given to using butyl acetate.

In the case of PVD metal pigments or in the case of particularly thin metal pigments produced by wet grinding, the drying step iii. will be dispensed with and these pigments will instead be left in a dispersion.

A portion of the additives used will not adhere to the surface of the effect pigment as the surface is already saturated. For high and uniform coverage, however, it is important to provide sufficient amounts of additive since only then can a strong leafing effect be expected.

In the nail varnish compositions of the invention, the surface-modified effect pigments preferably adopt an ordered arrangement at the surface of the clearcoat, i.e. of the nail varnish composition of the invention without surface-modified effect pigments. According to the invention, "adopt an ordered arrangement at the surface" means that the surface-modified effect pigments, on the nail varnish base and/or proceeding from the nail varnish composition/air or nail varnish composition/overcoat interface, are in the third of the nail varnish composition that adjoins this interface in the direction of the varnished substrate. Preferably, the surface-modified effect pigments float in the clearcoat and become aligned at the clearcoat surface. The surface-modified effect pigments therefore show marked leafing characteristics in the nail varnish composition of the invention.

Due to these marked leafing characteristics of the surface-modified effect pigments, it is possible in accordance with the invention to produce nail varnish compositions that owe their visual appearance mainly to the at least one surface-modified effect pigment added to the nail varnish base. Depending on the at least one surface-modified effect pigment, nail varnish compositions which, after application and drying, are notable for their metallic character, their mother-of-pearl-like shimmer, their interference color, a color change at different viewing angles, intense sparkle effects and/or silky appearance, to name just a few effects achievable by way of example, are thus obtainable in a simple manner. It is of course possible, according to the visual effect to be achieved, to also add various surface-modified effect pigments to the nail varnish composition, it being possible here for both the surface modification and the effect pigments to be different from one another. "Effect pigments different from one another" are also understood to mean effect pigments that are identical by nature, for example aluminum pigments, but differ from one another in terms of their particle size, for example.

A peculiarity that should also be mentioned in the case of use of surface-modified effect pigments based on aluminum platelets or based on metallic silver-coated nonmetallic substrates in platelet form is that it is possible thereby to obtain, after application and drying, nail varnish compositions having specular gloss. In the ideal case, the nail varnish compositions of the invention in that case have, after application and drying, such high image sharpness that a viewer is virtually able to view a mirror image therein.

According to the invention, "specular gloss" is understood to mean that the nail varnish composition, after application to glass plates by means of a bar applicator (Erichsen System Wasag Model 288 film applicator, from Erichsen) in a wet film thickness of 110 µm and after subsequent drying at room temperature, has at least 120 gloss units, measured in the 20° geometry (Byk-Gardner, digital catalog "Qualitatskontrolle for Lacke und Kunststoffe" [Quality Control for Paints and Plastics], page 16) and at least 1100 haze units (H log). According to the invention, excellent specular gloss is understood to mean achievement of at least 150 gloss units, measured in the 20° geometry (Byk-Gardner, digital catalog "Qualitatskontrolle für Lacke und Kunststoffe", page 16) and at least 1100 haze units (H log). The gloss and haze units (H log) are preferably determined here with the haze-gloss instrument, from Byk-Gardner. If the nail varnish applications of the invention have microscopically small structures, light is scattered thereon close to the reflection angle, which reduces the image sharpness of the nail varnish applications. Gloss (20° geometry) and haze are preferably not considered independently of one another in the assessment of specular gloss. The higher the numerical value of the gloss units in the 20° geometry, the lower the numerical value of the haze units (H log) can be or vice versa; the higher the numerical value of the haze units (H log), the lower the numerical value of the gloss units in the 20° geometry can be in order still to be perceived as specular gloss by the human eye. The higher the numerical value of the gloss units in the 20° geometry and the higher the numerical value of the haze units (H log), the higher the visually perceptible image sharpness of the nail varnish application.

In a very preferred embodiment, the nail varnish compositions of the invention, after application to glass plates by means of a bar applicator (Erichsen System Wasag Model 288 film applicator, from Erichsen) in a wet film thickness of 110 µm and after subsequent drying at room temperature, have at least 200 gloss units, preferably at least 300 gloss units, more preferably at least 400 gloss units, most preferably at least 450 to 1500 gloss units, in each case measured in the 20° geometry, and at least 1200 haze units (H log), preferably at least 1300 haze units (H log), more preferably at least 1400 haze units (H log) and most preferably at least 1410 to 2000 haze units (H log). In this embodiment too, in the case of a relatively low numerical value of the gloss units, measured in the 20° geometry, preference is given to a relatively high numerical value of the haze units (H log).

In a preferred embodiment, the nail varnish compositions of the invention which, after application and drying, feature excellent specular gloss contain 0.4% by weight to 2.7% by weight, preferably 0.5% by weight to 1.8% by weight, based in each case on the total weight of the nail varnish composition, of surface-modified effect pigments based on aluminum platelets, where the aluminum platelets have a $D_{50}$ from a range from 2 µm to 500 µm, preferably from a range from 2.5 µm to 90 µm, and an average thickness from a range from 15 nm to 1000 nm, preferably from a range from 18 nm to 60 nm.

In a particularly preferred embodiment, the nail varnish compositions of the invention which, after application, feature excellent specular gloss contain 0.6% by weight to 4.9% by weight, preferably 0.3% by weight to 3.8% by weight, based in each case on the total weight of the nail varnish composition, of surface-modified effect pigments based on aluminum platelets, where the aluminum platelets have a $D_{50}$ from a range from 5 µm to 150 µm, preferably from a range from 10 µm to 60 µm, and an average thickness from a range from 10 nm to 600 nm, preferably from a range from 20 nm to 100 nm.

In a preferred embodiment, the nail varnish compositions of the invention after application to a glass plate by means of a bar applicator (Erichsen System Wasag Model 288 film applicator, from Erichsen) in a wet film thickness of 100 µm and subsequent drying at room temperature, have at least 200 gloss units, measured in the 20° geometry, and at least 1200 haze units (H log).

In a preferred embodiment, the nail varnish composition of the invention comprises at least one surface-modified effect pigment in a proportion from a range from 0.1% by weight to 8.4% by weight, preferably in a proportion from a range from 0.15% by weight to 6.9% by weight, more preferably in a proportion from a range from 0.2% by weight to 4.3% by weight, based in each case on the total weight of the nail varnish composition, of at least one hydrocarbon resin and at least one solvent.

In a further preferred embodiment, the nail varnish composition of the invention comprises at least one surface-modified effect pigment based on a metallic substrate in platelet form, where the effect pigment has an average particle size $D_{50}$ from a range from 2 µm to 60 µm and an average total thickness from a range from 10 nm to 150 nm.

Binder:

The nail varnish compositions of the invention comprise at least one hydrocarbon resin as binder, where the binder preferably has a binder solids content from a range from 25% by weight to 64% by weight, further preferably from a range from 25% by weight to 60% by weight, further preferably from a range from 28% by weight to 55% by weight, more preferably from a range from 29% by weight to 50% by weight and most preferably from a range from 35% by weight to 43% by weight, based in each case on the total weight of the nail varnish composition.

Below a binder content of 25% by weight, no good optical effects resulting from the effect pigments were any longer apparent in the nail varnish applied.

Above 60% by weight, the optical quality of the effect pigments likewise declines and the viscosity of the nail varnish compositions of the invention increasingly becomes too high.

The nail varnish compositions of the invention preferably comprise, as binder, hydrocarbon resins having an average molecular weight ($M_w$) from a range from 800 to 6000, preferably from a range of 900 to 5000, or from a range from 8000 to 10000, preferably from a range from 8500 to 9300. Average molecular weight $M_w$ was determined by means of gel permeation chromatography (GPC) with a polystyrene standard.

Hydrocarbon resins are understood to mean synthetic resins that form through reaction of hydrocarbons (excluding olefins) with themselves in the presence of aluminum chloride or sulfuric acid as catalyst. Hydrocarbon resins are subdivided in accordance with their structure into petroleum resins, terpene resins and coumarone-indene resins. Also counted among the hydrocarbon resins are the reaction products of xylene and formaldehyde, the xylene-formaldehyde resins.

Hydrocarbon resins are produced in a known manner by heating high-boiling fractions from gasoline pyrolysis (pyrolysis oil) or the isoprene-free $C_5$ fraction from gasoline pyrolysis in the presence of aluminum chloride. The hydrocarbon resins are soluble in most organic solvents, for example esters, ethers, hydrochlorocarbons and aromatics.

Without being bound to a theory, the inventors suspect that, in the case of use of polar binders, the effect pigments coated with suitable additives are still partly wetted by the binder and therefore do not have the desired leafing effect. By contrast, the resins in the nail varnish composition of the invention are very nonpolar and accordingly do not wet the effect pigments. As a result, the effect pigments can better develop the leafing effect.

In preferred embodiments, nail varnish compositions comprising aromatic hydrocarbon resins are used.

The nail varnish compositions of the invention may comprise, as binder, hydrocarbon resins such as, for example, Kristalex F100 Hydrocarbon Resin, Kristalex 5140 Hydrocarbon Resin, Kristalex 3070 Hydrocarbon Resin, Kristalex 3085 Hydrocarbon Resin, Kristalex F115 Hydrocarbon Resin, each from Eastman.

Preferably, the nail varnish compositions of the invention comprise, as binder, hydrocarbon resins Kristalex F100 Hydrocarbon Resin and Kristalex 5140 Hydrocarbon Resin.

In particularly preferred embodiments, the nail varnish composition of the invention contains hydrocarbon resin in an amount that makes up 80% to 100% by weight, further preferably 90% to 99% by weight, of the overall organic binder.

The use of hydrocarbon resins in nail varnishes as a main constituent of the binder is unusual to the inventors' knowledge. Hydrocarbon resins are usually very rare constituents of nail varnishes and, if they are used, they are used in comparatively small proportions with other binders.

In a particularly preferred embodiment, the nail varnish compositions of the invention comprise at least two different hydrocarbon resins having a first average molecular weight $M_w$ of 1200 to 1600 g/mol and a second average molecular weight $M_w$ of 4500 to 5500 g/mol in a weight ratio of 1:1 to 1:10, preferably 1:1 to 1:8, more preferably 1:1 to 1:4 and most preferably 1:1 to 1:2 of the two different hydrocarbon resins.

In further embodiments, the nail varnish composition contains virtually no additional binders, if any, from the group of nitrocellulose, polyester resins, polyvinyl resins, alkyd resin, epoxy resins or cellulose acetate butyrate. These binders are preferably present in proportions of below 10% by weight, further preferably below 5% by weight and more preferably of below 1% by weight and most preferably below 0.1% by weight, based in each case on the total weight of hydrocarbon resins and additional binders. These binders have been found to be a hindrance if anything to the achievement of a truly strong mirror effect.

Without being bound to a theory, the inventors suspect that, in nail varnish compositions that contain the abovementioned binders, these at least partly wet the effect pigments owing to their stronger polarity and as a result they have poorer leafing properties.

Solvent:

The nail varnish compositions of the invention preferably contain particular solvents. Solvents added to the nail varnish compositions of the invention may be ethyl acetate, butyl acetate, isopropanol.

Preferably, the nail varnish composition of the invention contains a mixture of isopropanol, ethyl acetate and butyl acetate as solvent.

More preferably, the nail varnish composition of the invention contains the solvent mixture of isopropanol, ethyl acetate and butyl acetate in an amount which makes up 70% to 100% by weight, further preferably 75% to 98% by weight, based on the total solvent in the nail varnish composition.

It is unimportant here whether these preferred solvents are introduced by the binders or the effect pigment dispersion.

In further preferred embodiments, in this solvent mixture, the ratio of butyl acetate to the solvent mixture is 50% to 99% by weight and more preferably 55% to 98.5% by weight.

In a further particularly preferred embodiment, the proportion of isopropanol is below 20% by weight, preferably below 15% by weight, and further preferably below 10% by weight, based in each case on the total solvent.

Excessively high proportions of isopropanol in the nail varnish composition of the invention lead to a poor visual appearance of the effect pigments. This is probably attributable to excessively rapid drying of the nail varnishes after application thereof.

In a further particularly preferred embodiment, the nail varnish composition of the invention comprises at least one surface-modified effect pigment based on a metallic substrate in platelet form, at least two different hydrocarbon resins, and the solvents ethyl acetate, butyl acetate, isopropanol.

The nail varnish compositions of the invention are applicable in an extremely simple manner to a human or synthetic fingernail and/or toenail. During application, they are notable for good leveling and, after subsequent drying, form a homogeneous film on a human or synthetic fingernail and/or toenail.

In preferred embodiments, the nail varnish of the invention contains 50% by weight to 70% by weight, preferably 55% by weight to 68% and more preferably 57% to 65% by weight of solvent, based in each case on the weight of the overall nail varnish.

Below 55% by weight, there is an excessively significant rise in the viscosity of the nail varnish and the effect pigments are unable to adopt an optimal orientation, which leads to a reduction in up to loss of specular gloss.

Above 70% by weight, there is a reduction in the viscosity of the nail varnish, which leads to poorly controllable application of the nail varnish to the fingernail.

Further Constituents:

The nail varnish compositions of the invention may additionally contain one or more further constituents. Particular mention should be made here of plasticizers and antioxidants.

Plasticizers used may, for example, be glycols and derivatives thereof, for example diethylene glycol ethyl ether, diethylene glycol methyl ether, diethylene glycol butyl ether or additionally diethylene glycol hexyl ether, ethylene glycol ethyl ether, ethylene glycol methyl ether, ethylene glycol butyl ether, ethylene glycol hexyl ether, glycol esters, derivatives of propylene glycol and especially propylene glycol phenyl ether, propylene glycol diacetate, dipropylene glycol butyl ether, tripropylene glycol butyl ether, propylene glycol methyl ether, dipropylene glycol ethyl ether, tripropylene glycol methyl ether and diethylene glycol methyl ether, propylene glycol butyl ether, or mixtures thereof.

In addition, plasticizers used may especially be esters of carboxylic acids, for example of citrates, especially trimethyl citrate, tributyl citrate, trimethylacetyl citrate, tributylacetyl citrate, tri-2-ethylhexyl acetyl citrates or of phthalates, especially dimethoxyethyl phthalate; or of phosphates, especially tricresyl phosphate, tributyl phosphate, triphenyl phosphate, tributoxyethyl phosphates or of tartrates, especially dibutyl tartrate; adipates, carbonates, sebacates; benzyl benzoate, butyl acetyl ricinoleate, glyceryl acetyl ricinoleate, butyl glycolate, camphor, glycerol triacetate, N-ethyl-o,p-toluenesulfonamide, oxyethylene compounds, for example oxyethylene oils, especially vegetable oils, for example castor oil, hydrocarbon oils and mixtures thereof.

Preferred plasticizers are especially hydrocarbon oils.

The proportions by weight of the plasticizers in the overall nail varnish composition are preferably a range from 0% to 15% by weight, further preferably from 1% to 10% by weight, and more preferably from 5% to 10% by weight.

Antioxidants:

The nail varnish composition of the invention may additionally contain one or more antioxidants.

"Antioxidants" are understood to mean compounds that protect the constituents of the nail varnish of the invention, especially the hydrocarbon binders, from the effect of oxygen, heat, ozone and/or UV radiation. It is possible to use one or more compounds of this kind. Examples of compounds of this kind are IRGANOX® 1010, IRGANOX® 565, IRGANOX® 1076 (from BASF) or sulfur-containing antioxidants, for example zinc dibutyldithiocarbamate (PERKACIT ZDBC (from Performance additives Italy S.p.A)).

The antioxidants are preferably used in amounts from a range from 0% to 5% by weight, further preferably from a range from 0.05% to 1% by weight, based on the overall nail varnish composition.

Further Additives:

The nail varnish composition of the invention may additionally contain customary further additives as known to those skilled in the art.

Further additives of this kind are, for example, antisettling agents, preservatives, oils, waxes, free-moiety scavengers, wetting additives, dispersing aids, wetting aids, antifoams, perfume, neutralizing agents, thickeners, UV blockers, humectants, vitamins, proteins and mixtures thereof.

In further embodiments, the nail varnish composition of the invention preferably does not contain any antisettling agents. Astonishingly, any surface-modified effect pigment that has settled out can generally be redispersed by simply shaking even without the addition of antisettling agents.

The nail varnish composition of the invention preferably has a viscosity of 10 sec to 16 sec, measured with a DIN flow cup (DIN 4 mm) according to DIN 53211.

In preferred embodiments, the nail varnish composition of the invention contains aluminum PVD effect pigments having an average thickness $h_{50}$ from a range from 14 to 40 nm, preferably from a range from 15 to 35 nm, which have been coated with phosphoric acid cetyl ester or laurylphosphonic acid as leafing additive, aromatic hydrocarbon resins as binder and a mixture of isopropanol, ethyl acetate and butyl acetate as solvent, where this solvent mixture makes up 70% to 100% by weight of the total solvent in the nail varnish composition.

In a further preferred embodiment, the nail varnish composition of the invention contains aluminum PVD effect pigments having an average thickness $h_{50}$ from a range from 14 to 40 nm, preferably from a range from 15 to 35 nm, and also at least two different aromatic hydrocarbon resins and a mixture of isopropanol, ethyl acetate and butyl acetate as solvent, where this solvent mixture makes up 70% to 100% by weight of the total solvent in the nail varnish composition. Here too, leafing additives used are preferably phosphoric acid cetyl ester or laurylphosphonic acid.

The invention further provides a process for producing the nail varnish composition of the invention, comprising the steps of i) surface-modifying the effect pigment by means of an additive in a dispersion in a solvent, ii) dissolving the hydrocarbon resin in a solvent or solvent mixture, iii) mixing and homogenizing the dispersion according to i) with the binder solution according to ii).

Preference is given here to executing step i) as per claim 3.

The dissolving of the hydrocarbon resin in a solvent is preferably effected in a mixture of at least two, preferably three, solvents. Particular preference is given to using a mixture of isopropanol, ethyl acetate and butyl glycol.

In further preferred embodiments, the solvent in step i) will likewise consist of isopropanol, ethyl acetate and butyl glycol or a mixture of these, in order not to introduce further, possibly disruptive solvents into the nail varnish.

It is further preferable, in the selection of the metallic effect pigments, to choose those that are in a paste or a dispersion of the preferred solvents isopropanol, ethyl acetate and butyl glycol, since the solvent in the metal effect pigment paste likewise gets into the nail varnish of the invention in small amounts unless complex rewetting steps are used.

The invention likewise provides a method of coating a natural or synthetic fingernail, comprising the steps of:

a) coating the natural or synthetic fingernail with a nail varnish composition of the invention and then drying the nail varnish, b) optionally subsequently coating the nail varnish with a clearcoat.

The application of the clearcoat considerably increases the abrasion resistance of the nail varnish. Owing to the marked leafing effect of the effect pigments in the nail varnish, it naturally has comparatively low abrasion resistance.

Step a) may likewise be preceded by coating of the natural or synthetic fingernail with a clearcoat in order to establish a very even surface. This course of action is advisable if the fingernails have high roughness.

The subsequent coating with clearcoat in step b) can be conducted with the same clearcoat as or a different clearcoat than the nail varnish of the invention. However, this clearcoat in no case contains effect pigments since these would cover over the desired effect of the nail varnish of the invention.

However, the clearcoat in step b) may contain conventional color pigments or dyes. Specifically in combination with metallic PVD aluminum pigments or with thin aluminum effect pigments produced by wet grinding and having an $h_{50}$ of 20 to below 100 nm, it is possible to achieve very visually appealing effects. In this case, the nail varnish compositions of the invention that have been pigmented with the effect pigments preferably have specular gloss after step a).

In a further embodiment, the nail varnish composition of the invention may be overcoated with a low-viscosity UV-curing clearcoat in order to increase the abrasion resistance of the nail varnish composition of the invention.

It is also possible with preference to use solvent-based clearcoats. Without being bound to a theory, the clearcoat is preferably based on polar binders that interact only to a minor degree with the hydrocarbon resins of the clearcoat of the invention. In particularly preferred embodiments, these clearcoats are based on binders such as polyvinyl butyral (PVB), polyvinylpyrrolidone (PVP) or mixtures thereof.

In addition, the clearcoat preferably contains solvents that do not (partly) dissolve the nonpolar hydrocarbon resins of the varnish of the invention. For example, isopropanol may be used for this purpose. Otherwise, the leafing effect pigments can also be partly dissolved again and their orientation can be disrupted, which disrupts the specular gloss effect.

Surprisingly, the clearcoats of the invention have very good bond strength on the nail varnish of the invention.

In a further aspect of the invention, the surface-modified effect pigments as claimed in claim 1 or 2 can be used in further cosmetic applications. Examples of these include body powders, face powders, pressed or loose powders, powder creams, eye makeup, for example eyeshadow, mascara, eyeliner, liquid eyeliner, eyebrow pencil, lip pencil, lipstick, lip gloss, lip liner, hairstyling compositions such as hairspray, hair mousse, hair gel, hair wax, hair mascara, permanent or semipermanent hair dyes, temporary hair dyes or skincare compositions such as lotions, gels, emulsions.

The surface-modified effect pigments of the invention are combined here with raw materials, auxiliaries and active ingredients suitable for the respective application. The total concentration of surface-modified effect pigments of the invention in the cosmetic formulation may be between 0.001% by weight for rinse-off products and 40.0% by weight for leave-on products, based in each case on the total weight of the formulation.

EXAMPLES

The examples which follow serve for further description of the invention and are not supposed to be restrictive in any way. All percentages are percentages by weight. The terms NVC (nonvolatile content), proportion of solids and solids content are usable interchangeably.

I Production of the Surface-Modified Effect Pigments of the Invention that are to be Used with Preference in a Nail Varnish Composition and Production of the Surface-Modified Effect Pigments as Claimed in Claim 1

Examples 1 to 7

In a 1 L jacketed reactor, 300 g of the aluminum effect pigment METALURE A 41010 AE (dispersion in ethyl acetate, solids content 10%, $D_{50}$ (Horiba LA-930)=9.5 μm to 10.5 μm, from ECKART GmbH) in a solvent according to table 2 below were dispersed at 200 rpm/min and heated to 40° C. Subsequently, the phosphoric acid cetyl ester additive (CAS number: 3539-43-3, Hostaphat CC 100, from Clariant) according to table 2 below, dissolved in 30 g of the solvent used for dispersion, was added to the aluminum effect pigment dispersion. After stirring at 90° C. for 6 hours, the mixture was cooled down and filtered through a Bichner funnel. Surface-modified aluminum effect pigments were obtained in the form of 5-25% dispersions, which, after incorporation into the clearcoat according to IIa (pigmentation level: 0.4% by weight, based on total weight of the clearcoat), application to a synthetic fingernail and subsequent drying, gave a nail varnish having mirror-like gloss.

TABLE 2

| Example | Solvent | Amount of solvent [g] | Amount of additive [g] | NVC [%][1] |
|---|---|---|---|---|
| 1 | butyl acetate 85/100 | 0 | 3 | 10 |
| 2 | butyl acetate 85/100 | 50 | 3 | 9 |
| 3 | butyl acetate 85/100 | 100 | 3 | 11 |
| 4 | butyl acetate 85/100 | 200 | 3 | 7 |
| 5 | butyl acetate 85/100 | 300 | 3 | 23 |
| 6 | butyl acetate 85/100 | 300 | 6 | 21 |
| 7 | ethyl acetate | 200 | 5.4 | 6 |

[1]Nonvolatile content of the surface-modified effect pigment.

Examples 8 to 12

In a 1 L jacketed reactor, 300 g of the aluminum effect pigment METALURE A 41506 EN (dispersion in ethanol, solids content 15%, $D_{50}$ (Horiba LA-930)=5.5 μm to 6.5 μm, from ECKART GmbH) were dispersed in 300 g of solvent according to table 3 below at 200 rpm/min and heated to 40° C. Subsequently, the additive according to table 3 below in 30 g of the appropriate solvent was added to the aluminum effect pigment dispersion. After stirring at 90° C. for 6 hours, the mixture was cooled down and filtered through a Bichner funnel. Surface-modified aluminum effect pigments were obtained in each case in the form of a 10-20% dispersion, which, after incorporation into the clearcoat according to IIa (pigmentation level: 0.4% by weight, based on total weight of the clearcoat), application to a synthetic fingernail and subsequent drying, gave a nail varnish having mirror-like gloss.

TABLE 3

| Example | Solvent | Additive | Amount [g] | NVC [%] |
|---|---|---|---|---|
| 8 | butyl acetate 85/100 | Hostaphat CC 100[2] | 3 | 18 |
| 9 | butyl acetate 85/100 | Hostaphat CC 100 | 6 | 15 |
| 10 | methoxypropanol | Hostaphat CC 100 | 9 | 18 |
| 11 | methoxypropanol | laurylphosphonic acid[3] | 6 | 14 |
| 12 | butyl acetate 85/100 | laurylphosphonic acid | 6 | 15 |

[2]Phosphoric acid cetyl ester, CAS number: 3539-43-3, from Clariant.
[3]From Rhodia.

Example 13

In a 1 L jacketed reactor, 300 g of the aluminum effect pigment METALURE A 41010 AE (dispersion in ethyl acetate, solids content 10%, $D_{50}$ (Horiba LA-930)=9.5 μm to 10.5 μm, from ECKART GmbH) were dispersed in 50 g of butyl acetate 85/100 at 200 rpm/min and heated to 80° C. Subsequently, 3 g of the phosphoric acid cetyl ester additive (CAS number: 3539-43-3, Hostaphat CC 100, from Clariant) in 30 g of butyl acetate 85/100 were added to the aluminum effect pigment dispersion. After stirring at 40° C. for 6 hours, the mixture was cooled down and filtered through a Bichner funnel. A surface-modified aluminum effect pigment was obtained in the form of a 15% dispersion, which, after incorporation into the clearcoat according to IIa (pigmentation level: 0.4% by weight, based on total weight of the clearcoat), application to a synthetic fingernail and subsequent drying, gave a nail varnish with mirror-like gloss.

Example 14

In a 1 L jacketed reactor, 300 g of the aluminum effect pigment METALURE A 41010 AE (dispersion in ethyl acetate, solids content 10%, $D_{50}$ (Horiba LA-930)=9.5 μm to 10.5 μm, from ECKART GmbH) were dispersed in 50 g of butyl acetate 85/100 at 200 rpm/min and heated to 60° C. Subsequently, 3 g of the phosphoric acid cetyl ester additive (CAS number: 3539-43-3, Hostaphat CC 100, from Clariant) in 30 g of butyl acetate 85/100 were added to the aluminum effect pigment dispersion. After stirring at 40° C. for 6 hours, the mixture was cooled down and filtered through a Bichner funnel. A surface-modified aluminum effect pigment was obtained in the form of a 10% dispersion, which, after incorporation into the clearcoat according to IIa (pigmentation level: 0.4% by weight, based on total weight of the clearcoat), application to a synthetic fingernail and subsequent drying, gave a nail varnish with mirror-like gloss.

Examples 15 to 18

In a 1 L jacketed reactor, 300 g of effect pigment according to table 4 below were dispersed in 300 g of solvent according to table 4 below at 200 rpm/min and heated to 90° C. Subsequently, the phosphoric acid cetyl ester additive (CAS number: 3539-43-3, Hostaphat CC 100, from Clariant) in 30 g of the appropriate solvent was added to the effect pigment dispersion. After stirring at 40° C. for 6 hours, the mixture was cooled down and filtered through a Bichner funnel. Surface-modified effect pigments were obtained in each case as a dispersion which, after incorporation into the clearcoat according to IIa (pigmentation level: 0.4% by weight, based on total weight of the clearcoat), application to a synthetic fingernail and subsequent drying, gave a nail varnish, the visual appearance of which was attributable to the effect pigment used in each case.

TABLE 4

| Example | Effect pigment | Additive [g] | Solvent | NVC [%] |
|---|---|---|---|---|
| 15 | SILVERSHINE S 1500[4] | 3 | monopropylene glycol monomethyl ether[8] | 35 |
| 17 | SYNCRYSTAL Silk Blue[5] | 3 | monopropylene glycol monomethyl ether | 72 |
| 17 | METALURE A 31017 AE[6] | 3 | butyl acetate 85/100 | 12 |
| 18 | METALURE A 31017 AE[6] | 6 | butyl acetate 85/100 | 12 |

[4]Aluminum effect pigment paste, solids content 23% to 27%, $D_{50}$ (CILAS 1064) = 12 μm to 18 μm, from ECKART GmbH.
[5]Titanium dioxide-coated pearlescent pigment with blue interference color, $D_{50}$ (Malvern Mastersizer 2000) = 13 μm, from ECKART GmbH.
[6]Aluminum effect pigment, dispersion in ethyl acetate, solids content 10%, $D_{50}$ (Horiba LA-930) = 17 μm, from ECKART GmbH.

Examples 19 to 24

In a 1 L jacketed reactor, 300 g of the aluminum effect pigment METALURE L 55350 AE (dispersion in ethyl acetate, solids content 10%, $D_{50}$ (Horiba LA-930)=11 μm to 12 μm, from ECKART GmbH) were dispersed in 300 g of solvent according to table 5 below at 200 rpm/min and heated to 40° C. Subsequently, the additive used in each case in 30 g of butyl acetate 85/100 was added to the aluminum effect pigment dispersion. After stirring at 100° C. for 6 hours, the mixture was cooled down and filtered through a Bichner funnel. Surface-modified aluminum effect pigments were obtained in each case in the form of a 11-20% dispersion, which, after incorporation into the clearcoat according to IIa (pigmentation level: 0.4% by weight, based on total weight of the clearcoat), application to a synthetic fingernail and subsequent drying, gave a nail varnish with mirror-like gloss.

TABLE 5

| Example | Additive | Solvent | Amount [g] | NVC [%] |
|---|---|---|---|---|
| 19 | laurylphosphonic acid | butyl acetate 85/100 | 3 | 18 |
| 20 | laurylphosphonic acid | butyl acetate 85/100 | 6 | 18 |
| 21 | laurylphosphonic acid | monopropylene glycol monomethyl ether | 6 | 18.5 |
| 22 | Hostaphat CS 120[6] | butyl acetate 85/100 | 6 | 15 |
| 23 | Hostaphat CS 120 | butyl acetate 85/100 | 15 | 15 |
| 24 | Hostaphat CC 100 | butyl acetate 85/100 | 3 | 11.7 |

[6]Phosphoric acid stearyl ester, CAS number: 39471-52-8, from Clariant.

Examples 25 to 31, Comparative Example 1

In a 1 L jacketed reactor, 200 g of Silverdream Moonlight 501 L (solids content 50%, $D_{50}$ (CILAS 1064)=15 μm to 20 μm, from ECKART GmbH) were dispersed in 525 g of butyl acetate 85/100 at 200 rpm/min and heated to 40° C. Subsequently, the additive used according to table 6 in 30 g of butyl acetate 85/100 was added to the aluminum effect pigment dispersion. After stirring at 90° C. for 6 hours, the mixture was cooled down and filtered through a Bichner funnel. Surface-modified aluminum effect pigments were obtained in the form of a 45-60% dispersion, which, after incorporation into the clearcoat according to IIa (pigmentation level: 0.4% by weight, based on total weight of the clearcoat), application to a synthetic fingernail and subsequent drying, in the case of use of the surface-modified aluminum effect pigments from examples 26 to 32 gave a nail varnish having mirror-like gloss, or in the case of use of the surface-modified aluminum effect pigment from comparative example 1 gave a nail varnish without mirror-like gloss, with a matt aluminum gray hue.

TABLE 6

| Example/ comparative example | Additive | Amount [g] | NVC [%] |
|---|---|---|---|
| Example 25 | Hostaphat CC 100 | 2.5 | 50 |
| Example 26 | Hostaphat CC 100 | 5 | 53 |
| Example 27 | Hostaphat CC 100 | 7.5 | 53 |
| Example 28 | Hostaphat CC 100 | 20 | 61 |
| Example 29 | Hostaphat CS 120 | 5 | 55 |
| Example 30 | Hostaphat CS 120 | 10 | 53 |
| Example 31 | Amphisol[7] | 10 | 46 |
| Comparative example 1 | Hostaphat CS 120 | 20 | 58 |

[7]1-Hexadecanol phosphate, 2,2'-iminobis[ethanol] 1:1, CAS 69331-39-1, from DSM.

Comparative Examples 2 to 8

In a 1 L jacketed reactor, 300 g of the aluminum effect pigment METALURE L 55350 AE (dispersion in ethyl acetate, solids content 10%, $D_{50}$ (Horiba LA-930)=11 μm to 12 μm, from ECKART GmbH) were dispersed in 300 g of butyl acetate 85/100 at 200 rpm/min and heated to 100° C. Subsequently, the additive used according to table 7 in 30 g of butyl acetate 85/100 was added to the aluminum effect pigment dispersion. After stirring at 40° C. for 6 hours, the mixture was cooled down and filtered through a Bichner funnel. Surface-modified aluminum effect pigments were each obtained in the form of a 10-20% dispersion, which, after incorporation into the clearcoat according to IIa (pigmentation level: 0.4% by weight, based on total weight of the clearcoat), application to a synthetic fingernail and subsequent drying, gave a nail varnish without mirror-like gloss, but rather a nail varnish with a matt aluminum gray hue.

TABLE 7

| Comparative example | Additive | Amount [g] | NVC [%] |
|---|---|---|---|
| 2 | SilCare Silicone 41M80[8] | 3 | 18 |
| 3 | SilCare Silicone 41M80 | 15 | 15 |
| 4 | Hostaphat KW 340 D[9] | 3 | 13 |
| 5 | Hostaphat KW 340 D | 15 | 13 |
| 6 | Hostaphat KL 340 D[10] | 3 | 16 |
| 7 | Hostaphat KL 340 D | 15 | 14 |
| ~~8~~ | ~~Hostaphat CC 100~~ | ~~12~~ | ~~13~~ |

[8]INCI: C24-28 Alkyl Dimethicone, CAS number: 192230-29-8, from Aako BV or from Clariant.
[9]Mono-, di- and tri(alkyl tetraglycol ether) o-phosphoric ester, CAS number: 119415-05-3, from Clariant.
[10]Mono-, di- and tri(alkyl tetraglycol ether) o-phosphoric ester, CAS number: 121158-63-2; 121158-61-0; 121158-62-1, from Clariant.

Comparative Examples 9 to 11

In a 1 L jacketed reactor, 300 g of Silverdream Moonlight 501 L (solids content 50%. $D_{50}$ (CILAS 1064)=15 μm to 20

µm, from ECKART GmbH) were dispersed in 470 g of butyl acetate 85/100 at 200 rpm/min and heated to 90° C. Subsequently, the additive used in table 8 in 30 g of butyl acetate 85/100 was added to the aluminum effect pigment dispersion. After stirring at 40° C. for 6 hours, the mixture was cooled down and filtered through a Bichner funnel. Surface-modified aluminum effect pigments were obtained in the form of a 55-65% dispersion, which, after incorporation into the clearcoat according to IIa (pigmentation level: 1.5% by weight, based on total weight of the clearcoat), application to a synthetic fingernail and subsequent drying, gave a nail varnish without mirror-like gloss and/or without leafing effect.

TABLE 8

| Comparative example | Additive | Amount [g] | NVC [%] |
|---|---|---|---|
| 8 | Hostaphat CK 100[11] | 7.5 | 59 |
| 9 | Hostaphat CK 100 | 15 | 61 |
| 10 | Hostaphat CK 100 | 30 | 59 |
| 11 | Hostaphat CC 100 | 75 | 57 |

[11]Potassium hexadecylhydrogenphosphate, CAS 19035-79-1, Hostaphat CK 100; from Clariant.

Comparative Example 12

PVD aluminum pigment dispersion in ethyl acetate METALURE A-41010 AE, from ECKART GmbH, NVC: 10%, $D_{50}$=9.50 µm to 10.50 µm.

Comparative Example 13

PVD aluminum pigment dispersion in ethyl acetate METALURE L-55350 AE, from ECKART GmbH, NVC: 10%, $D_{50}$=11.00 µm to 12.00 µm.

Comparative Example 14

PVD aluminum pigment dispersion in ethyl acetate METALURE A-31017 AE, from ECKART GmbH, NVC: 10%, $D_{50}$=9.50 to 10.50 µm.

Comparative Example 15

Aluminum pigment paste SILVERSHINE S2100, from ECKART GmbH, NVC: 48.0% to 52.0%, $D_{50}$=17.0 µm to 23.0 µm.

Comparative Example 16

Mixture of 13% by weight of METALURE A-41010 AE, from ECKART GmbH and 0.2% by weight of Hostaphat CS 120, from Clariant.

II Production of the Nail Varnish Compositions of the Invention

IIa Production of the Clearcoat:

In a suitable stirred vessel, a 70% by weight binder solution F100 was produced. For this purpose, 70 g of the binder Kristalex F100 Hydrocarbon Resin (from Eastman) were added to an initial charge of 30 g of butyl acetate 98/100 while stirring and cooling (12° C.) with the Dispermat CNf2 dissolver (from Getzmann GmbH), and then the mixture was stirred at 3000 to 4000 rpm/min for a further 30 minutes.

In a second suitable stirred vessel, a 60% by weight binder solution 5140 was produced. For this purpose, 60 g of the binder Kristalex 5140 Hydrocarbon Resin (from Eastman) were added to an initial charge of 40 g of butyl acetate 98/100 while stirring and cooling (12° C.) with the Dispermat CNf2 dissolver (from Getzmann GmbH), and then the mixture was stirred at 3000 to 4000 rpm/min for a further 30 minutes.

The nonvolatile content (binder solids content) of the above-described binder solutions was determined according to DIN EN ISO 3251:2008.

For production of the clearcoat, the 70% by weight binder solution F100 and the 60% by weight binder solution 5140 were combined according to the table below while stirring at 900 rpm/min with the IKA RW 20 Digital laboratory stirrer (from IKA) at room temperature and stirred for a further 5 to 10 minutes. Subsequently, the solvents according to the respective table below were added successively while stirring at 600 rpm/min.

IIb Production of the Nail Varnish Compositions of the Invention

For production of the inventive nail varnish compositions of examples 32 to 35, 96 g of the clearcoat were added to an initial charge of 4 g of the respective surface-modified effect pigment according to tables 9, 10 and 11 below with stirring at 600 rpm/min.

TABLE 9

The inventive nail varnish compositions of examples 32 to 35 had a binder solids content of 30% by weight, based on the total weight of the clearcoat.

| Example | | Product name | Weight (g) | Weight ratio |
|---|---|---|---|---|
| Example 32 | Clearcoat | Kristalex F100 Hydrocarbon Resin, 70% by weight in butyl acetate | 22.3 | Kristalex F100 Hydrocarbon Resin:Kristalex 5140 Hydrocarbon Resin |
| | | Kristalex 5140 Hydrocarbon Resin, 60% by weight in butyl acetate | 26.0 | 1:1 |
| | | Isopropanol | 5.0 | |
| | | Ethyl acetate | 18.7 | |
| | | Butyl acetate 98/100 | 28.0 | |
| | | Effect pigment according to example 5, NVC: 23% | 4.0 | |

TABLE 9-continued

The inventive nail varnish compositions of examples 32 to 35 had a binder solids content of 30% by weight, based on the total weight of the clearcoat.

| Example | | Product name | Weight (g) | Weight ratio |
|---|---|---|---|---|
| Example 33 | Clearcoat | Kristalex F100 Hydrocarbon Resin, 70% by weight in butyl acetate | 14.8 | Kristalex F100 Hydrocarbon Resin:Kristalex 5140 Hydrocarbon Resin |
| | | Kristalex 5140 Hydrocarbon Resin, 60% by weight in butyl acetate | 34.6 | 1:2 |
| | | Isopropanol | 4.5 | |
| | | Ethyl acetate | 19.0 | |
| | | Butyl acetate 98/100 | 27.5 | |
| | | Effect pigment according to example 5, NVC: 23% | 4.0 | |
| Example 34 | Clearcoat | Kristalex F100 Hydrocarbon Resin, 70% by weight in butyl acetate | 8.9 | Kristalex F100 Hydrocarbon Resin:Kristalex 5140 Hydrocarbon Resin |
| | | Kristalex 5140 Hydrocarbon Resin, 60% by weight in butyl acetate | 41.6 | 1:4 |
| | | Isopropanol | 4.5 | |
| | | Ethyl acetate | 19.0 | |
| | | Butyl acetate 98/100 | 26.0 | |
| | | Effect pigment according to example 5, NVC: 23% | 4.0 | |
| Example 35 | Clearcoat | Kristalex F100 Hydrocarbon Resin, 70% by weight in butyl acetate | 4.8 | Kristalex F100 Hydrocarbon Resin:Kristalex 5140 Hydrocarbon Resin |
| | | Kristalex 5140 Hydrocarbon Resin, 60% by weight in butyl acetate | 46.3 | 1:8 |
| | | Isopropanol | 4.5 | |
| | | Ethyl acetate | 17.9 | |
| | | Butyl acetate 98/100 | 26.5 | |
| | | Effect pigment according to example 5, NVC: 23 | 4.0 | |

TABLE 10

The inventive nail varnish compositions of examples 36 to 39 had a binder solids content of 40% by weight, based on the total weight of the clearcoat.

| Example | | Product name | Weight (g) | Weight ratio |
|---|---|---|---|---|
| Example 36 | Clearcoat | Kristalex F100 Hydrocarbon Resin, 70% by weight in butyl acetate | 27.9 | Kristalex F100 Hydrocarbon Resin:Kristalex 5140 Hydrocarbon Resin |
| | | Kristalex 5140 Hydrocarbon Resin, 60% by weight in butyl acetate | 32.5 | 1:1 |
| | | Isopropanol | 3.0 | |
| | | Ethyl acetate | 11.6 | |
| | | Butyl acetate 98/100 | 25.0 | |
| | | Effect pigment according to example 5, NVC: 23% | 4.0 | |
| Example 37 | Clearcoat | Kristalex F100 Hydrocarbon Resin, 70% by weight in butyl acetate | 19.8 | Kristalex F100 Hydrocarbon Resin:Kristalex 5140 Hydrocarbon Resin |
| | | Kristalex 5140 Hydrocarbon Resin, 60% by weight in butyl acetate | 46.3 | 1:2 |
| | | Isopropanol | 3.1 | |
| | | Ethyl acetate | 12.3 | |
| | | Butyl acetate 98/100 | 18.5 | |
| | | Effect pigment according to example 5, NVC: 23% | 4.0 | |

TABLE 10-continued

The inventive nail varnish compositions of examples 36 to 39 had a binder solids content of 40% by weight, based on the total weight of the clearcoat.

| Example | | Product name | Weight (g) | Weight ratio |
|---|---|---|---|---|
| Example 38 | Clearcoat | Kristalex F100 Hydrocarbon Resin, 70% by weight in butyl acetate | 11.8 | Kristalex F100 Hydrocarbon Resin:Kristalex 5140 Hydrocarbon Resin |
| | | Kristalex 5140 Hydrocarbon Resin, 60% by weight in butyl acetate | 55.4 | 1:4 |
| | | Isopropanol | 2.9 | |
| | | Ethyl acetate | 11.9 | |
| | | Butyl acetate 98/100 | 20.0 | |
| | | Effect pigment according to example 5, NVC: 23% | 4.0 | |
| Example 39 | Clearcoat | Kristalex F100 Hydrocarbon Resin, 70% by weight in butyl acetate | 6.7 | Kristalex F100 Hydrocarbon Resin:Kristalex 5140 Hydrocarbon Resin |
| | | Kristalex 5140 Hydrocarbon Resin, 60% by weight in butyl acetate | 61.5 | 1:8 |
| | | Isopropanol | 2.9 | |
| | | Ethyl acetate | 11.5 | |
| | | Butyl acetate 98/100 | 17.4 | |
| | | Effect pigment according to example 5, NVC: 23% | 4.0 | |

TABLE 11

The inventive nail varnish compositions of examples 40 to 43 had a binder solids content of 60% by weight, based on the total weight of the clearcoat.

| Example | | Product name | Weight (g) | Weight ratio |
|---|---|---|---|---|
| Example 40 | Clearcoat | Kristalex F100 Hydrocarbon Resin, 70% by weight in butyl acetate | 42.9 | Kristalex F100 Hydrocarbon Resin:Kristalex 5140 Hydrocarbon Resin |
| | | Kristalex 5140 Hydrocarbon Resin, 60% by weight in butyl acetate | 50.0 | 1:1 |
| | | Isopropanol | 0.6 | |
| | | Ethyl acetate | 2.6 | |
| | | Butyl acetate 98/100 | 3.9 | |
| | | Effect pigment according to example 5, NVC: 23% | 4.0 | |
| Example 41 | Clearcoat | Kristalex F100 Hydrocarbon Resin, 70% by weight in butyl acetate | 28.6 | Kristalex F100 Hydrocarbon Resin:Kristalex 5140 Hydrocarbon Resin |
| | | Kristalex 5140 Hydrocarbon Resin, 60% by weight in butyl acetate | 66.7 | 1:2 |
| | | Isopropanol | 0.4 | |
| | | Ethyl acetate | 1.7 | |
| | | Butyl acetate 98/100 | 2.6 | |
| | | Effect pigment according to example 5, NVC: 23% | 4.0 | |
| Example 42 | Clearcoat | Kristalex F100 Hydrocarbon Resin, 70% by weight in butyl acetate | 17.1 | Kristalex F100 Hydrocarbon Resin:Kristalex 5140 Hydrocarbon Resin |
| | | Kristalex 5140 Hydrocarbon Resin, 60% by weight in butyl acetate | 80.0 | 1:4 |
| | | Isopropanol | 0.2 | |
| | | Ethyl acetate | 1.0 | |
| | | Butyl acetate 98/100 | 1.7 | |
| | | Effect pigment according to example 5, NVC: 23% | 4.0 | |
| Example 43 | Clearcoat | Kristalex F100 Hydrocarbon Resin, 70% by weight in butyl acetate | 9.6 | Kristalex F100 Hydrocarbon Resin:Kristalex 5140 Hydrocarbon Resin |
| | | Kristalex 5140 Hydrocarbon Resin, 60% by weight in butyl acetate | 88.8 | 1:8 |
| | | Isopropanol | 0.1 | |
| | | Ethyl acetate | 0.6 | |
| | | Butyl acetate 98/100 | 0.9 | |
| | | Effect pigment according to example 5, NVC: 23% | 4.0 | |

The visual appearance of the inventive nail varnish compositions of examples 32 to 43 was determined after application to a synthetic fingernail and subsequent drying by the surface-modified effect pigment from example 5 used in each case. The surface-modified effect pigment used in each case, in the clearcoat produced according to IIa, showed marked leafing characteristics and in some cases marked specular gloss. With regard to application characteristics, it was found that the nail varnish compositions of the invention with a binder solids content of 60% by weight, based on the total weight of the clearcoat, owing to their high viscosity, have poorer applicability than the nail varnish applications of the invention with a binder solids content of 30% by weight or 40% by weight, based in each case on the total weight of the clearcoat.

For the inventive nail varnish compositions of examples 44 to 48, the clearcoat was produced as described below under IIa. For production of the inventive nail varnish compositions of examples 44 to 48, 96 g of the clearcoat were added to an initial charge of 4 g of the respective surface-modified effect pigment according to table 12 below with stirring at 600 rpm/min.

TABLE 12

| Pigmentation, samples | | Product name | Weight (g) | Weight ratio |
|---|---|---|---|---|
| Example 44 | Clearcoat | Kristalex F100 Hydrocarbon Resin, 70% by weight in butyl acetate | 22.3 | Kristalex F100 Hydrocarbon Resin:Kristalex 5140 Hydrocarbon Resin |
| | | Kristalex 5140 Hydrocarbon Resin, 60% by weight in butyl acetate | 26.0 | 1:1 |
| | | Isopropanol | 4.7 | |
| | | Ethyl acetate | 19.0 | |
| | | Butyl acetate 98/100 | 28.0 | |
| | | Effect pigment according to example 5, NVC: 23% | 4.0 | |
| Example 45 | Clearcoat | Kristalex F100 Hydrocarbon Resin, 70% by weight in butyl acetate | 22.3 | Kristalex F100 Hydrocarbon Resin:Kristalex 5140 Hydrocarbon Resin |
| | | Kristalex 5140 Hydrocarbon Resin, 60% by weight in butyl acetate | 26.0 | 1:1 |
| | | Isopropanol | 4.7 | |
| | | Ethyl acetate | 19.0 | |
| | | Butyl acetate 98/100 | 28.0 | |
| | | Effect pigment according to example 5, NVC: 23% | 4.8 | |
| Example 46 | Clearcoat | Kristalex F100 Hydrocarbon Resin, 70% by weight in butyl acetate | 22.3 | Kristalex F100 Hydrocarbon Resin:Kristalex 5140 Hydrocarbon Resin |
| | | Kristalex 5140 Hydrocarbon Resin, 60% by weight in butyl acetate | 26.0 | 1:1 |
| | | Isopropanol | 4.7 | |
| | | Ethyl acetate | 19.0 | |
| | | Butyl acetate 98/100 | 28.0 | |
| | | Effect pigment according to example 5, NVC: 23% | 2.0 | |
| Example 47 | Clearcoat | Kristalex F100 Hydrocarbon Resin, 70% by weight in butyl acetate | 22.3 | Kristalex F100 Hydrocarbon Resin:Kristalex 5140 Hydrocarbon Resin |
| | | Kristalex 5140 Hydrocarbon Resin, 60% by weight in butyl acetate | 26.0 | 1:1 |
| | | Isopropanol | 4.7 | |
| | | Ethyl acetate | 19.0 | |
| | | Butyl acetate 98/100 | 28.0 | |
| | | Effect pigment according to example 5, NVC: 23% | 7.0 | |
| Example 48 | Clearcoat | Kristalex F100 Hydrocarbon Resin, 70% by weight in butyl acetate | 22.3 | Kristalex F100 Hydrocarbon Resin:Kristalex 5140 Hydrocarbon Resin |
| | | Kristalex 5140 Hydrocarbon Resin, 60% by weight in butyl acetate | 26.0 | 1:1 |
| | | Isopropanol | 4.7 | |
| | | Ethyl acetate | 19.0 | |
| | | Butyl acetate 98/100 | 28.0 | |
| | | Effect pigment according to example 5, NVC: 23% | 9.0 | |

For the inventive nail varnish compositions of examples 49 to 64, the clearcoat according to table 13 was produced as described above under IIa.

TABLE 13

Clearcoat for examples 49 to 64 and comparative examples 24 to 30

| | Product name | Weight (g) | Weight ratio |
|---|---|---|---|
| Clearcoat for examples 49 to 64 and comparative examples 26 to 33 | Kristalex F100 Hydrocarbon Resin, 70% by weight in butyl acetate | 19.8 | Kristalex F100 Hydrocarbon Resin:Kristalex 5140 Hydrocarbon Resin 1:2 |
| | Kristalex 5140 Hydrocarbon Resin, 60% by weight in butyl acetate | 46.3 | |
| | Isopropanol | 3.1 | |
| | Ethyl acetate | 12.3 | |
| | Butyl acetate 98/100 | 18.5 | |

For production of the inventive nail varnish compositions of examples 49 to 64, the clearcoat from table 13 was added according to table 14 below to an initial charge of the respective surface-modified effect pigment according to table 14, with stirring at 600 rpm/min. The inventive nail varnish compositions of examples 50 to 66 had a binder solids content of 40% by weight, based on the total weight of the clearcoat.

TABLE 14

Weights of effect pigment dispersion and clearcoat for examples 49 to 64.

| Example | Nail varnish composition | Weight (g) |
|---|---|---|
| 49 | Effect pigment according to example 1, NVC: 10% | 13.20 |
| | Clearcoat from table 13 | 86.80 |
| 50 | Effect pigment according to example 15, NVC: 35% | 3.80 |
| | Clearcoat from table 13 | 96.20 |
| 51 | Effect pigment according to example 14, NVC: 10% | 14.60 |
| | Clearcoat from table 13 | 85.40 |
| 52 | Effect pigment according to example 11, NVC: 14% | 9.65 |
| | Clearcoat from table 13 | 90.35 |
| 53 | Effect pigment according to example 12, NVC: 15% | 9.65 |
| | Clearcoat from table 13 | 90.35 |
| 54 | Effect pigment according to example 10; NVC: 18% | 7.65 |
| | Clearcoat from table 13 | 92.35 |
| 55 | Effect pigment according to example 21, NVC: 18.5% | 7.36 |
| | Clearcoat from table 13 | 92.64 |
| 56 | Effect pigment according to example 45, NVC: 11.7% | 11.64 |
| | Clearcoat from table 13 | 88.36 |
| 57 | Effect pigment according to example 17, NVC: 12% | 11.44 |
| | Clearcoat from table 13 | 88.56 |
| 58 | Effect pigment according to example 18, NVC: 12% | 11.44 |
| | Clearcoat from table 13 | 88.56 |
| 59 | Effect pigment according to example 5, NVC: 23% | 6.00 |
| | Clearcoat from table 13 | 94.00 |
| 60 | Effect pigment according to example 26, NVC: 53% | 2.60 |
| | Clearcoat from table 13 | 97.40 |
| 61 | Effect pigment according to example 28, NVC: 61% | 2.23 |
| | Clearcoat from table 13 | 97.70 |
| 62 | Effect pigment according to example 29, NVC: 55% | 2.47 |
| | Clearcoat from table 13 | 97.53 |
| 63 | Effect pigment according to example 25, NVC: 50% | 2.72 |
| | Clearcoat from table 13 | 97.28 |
| 64 | Effect pigment according to example 27, NVC: 53% | 2.57 |
| | Clearcoat from table 13 | 97.43 |

Comparative Examples

For the nail varnish compositions of comparative examples 17 to 20, the clearcoat was produced as described above under IIa. For production of the nail varnish compositions of comparative examples 18 to 20, 96 g of the clearcoat were added to an initial charge of 4 g of the respective surface-modified effect pigment according to table 15 below with stirring at 600 rpm/min.

TABLE 15

| Comparative example | Product name | Weight (g) | Weight ratio |
|---|---|---|---|
| Comparative example 17 | Clearcoat Kristalex F100 Hydrocarbon Resin, 70% by weight in butyl acetate | 22.25 | Kristalex F100 Hydrocarbon Resin:Kristalex 5140 Hydrocarbon Resin 1:1 |
| | Kristalex 5140 Hydrocarbon Resin, 60% by weight in butyl acetate | 26.0 | |
| | Isopropanol | 14.31 | |
| | Ethyl acetate | — | |
| | Butyl acetate 98/100 | 37.44 | |
| | Effect pigment according to example 5 | 4.0 | |

TABLE 15-continued

| Comparative example | | Product name | Weight (g) | Weight ratio |
|---|---|---|---|---|
| Comparative example 18 | Clearcoat | Kristalex F100 Hydrocarbon Resin, 70% by weight in butyl acetate | 19.13 | Kristalex F100 Hydrocarbon Resin:Kristalex 5140 Hydrocarbon Resin |
| | | Kristalex 5140 Hydrocarbon Resin, 60% by weight in butyl acetate | 19.13 | 1:1 |
| | | Isopropanol | 22.33 | |
| | | Ethyl acetate | 39.42 | |
| | | Butyl acetate 98/100 | — | |
| | | Effect pigment according to example 5 | 4.0 | |
| Comparative example 19 | Clearcoat | Kristalex F100 Hydrocarbon Resin, 70% by weight in butyl acetate | 14.87 | Kristalex F100 Hydrocarbon Resin:Kristalex 5140 Hydrocarbon Resin |
| | | Kristalex 5140 Hydrocarbon Resin, 60% by weight in butyl acetate | 34.63 | 1:2 |
| | | Isopropanol | 18.5 | |
| | | Ethyl acetate | 32.0 | |
| | | Butyl acetate 98/100 | — | |
| | | Effect pigment according to example 5 | 4.0 | |
| Comparative example 20 | Clearcoat | Kristalex F100 Hydrocarbon Resin, 70% by weight in butyl acetate | 14.9 | Kristalex F100 Hydrocarbon Resin:Kristalex 5140 Hydrocarbon Resin |
| | | Kristalex 5140 Hydrocarbon Resin, 60% by weight in butyl acetate | 34.69 | 1:2 |
| | | Isopropanol | 4.6 | |
| | | Ethyl acetate | 15.18 | |
| | | Butyl acetate 98/100 | 27.5 | |
| | | Acetone | 3.12 | |
| | | Effect pigment according to example 5 | 4.0 | |

The nail varnish compositions of comparative examples 17 to 20, after application to a synthetic fingernail and subsequent drying, showed a distinctly poorer visual appearance than the nail varnish compositions of the invention, which is probably attributable to the omission of one of the solvents (comparative example 17) and/or an excessively high relative proportion of the solvents isopropanol and/or ethyl acetate in relation to butyl acetate (comparative examples 18 and 19). Moreover, the addition of an additional solvent (acetone in comparative example 20) has an adverse effect. The nail varnish applications of the comparative examples were affected by white bloom and were cloudy, probably owing to excessively rapid drying. The exact compositions of the nail varnishes of the inventive examples and comparative examples can also be found in table 18.

For the nail varnish compositions of comparative examples 21 to 24, the clearcoat was produced as described above under IIa. For production of the nail varnish compositions of comparative examples 21 to 24, 96 g of the clearcoat were added to an initial charge of 4 g of the respective surface-modified effect pigment according to table 16 below with stirring at 600 rpm/min.

The nail varnish compositions of comparative examples 21 to 24 had a binder solids content of 20% by weight, based on the total weight of the clearcoat.

TABLE 16

| Comparative example | | Product name | Weight (g) | Weight ratio |
|---|---|---|---|---|
| Comparative example 21 | Clearcoat | Kristalex F100 Hydrocarbon Resin, 70% by weight in butyl acetate | 14.3 | Kristalex F100 Hydrocarbon Resin:Kristalex 5140 Hydrocarbon Resin |
| | | Kristalex 5140 Hydrocarbon Resin, 60% by weight in butyl acetate | 16.6 | 1:1 |
| | | Isopropanol | 6.3 | |
| | | Ethyl acetate | 25.1 | |
| | | Butyl acetate 98/100 | 37.9 | |
| | | Effect pigment according to example 5, NVC: 23% | 4.0 | |
| Comparative example 22 | Clearcoat | Kristalex F100 Hydrocarbon Resin, 70% by weight in butyl acetate | 9.6 | Kristalex F100 Hydrocarbon Resin:Kristalex 5140 Hydrocarbon Resin |
| | | Kristalex 5140 Hydrocarbon Resin, 60% by weight in butyl acetate | 22.2 | 1:2 |
| | | Isopropanol | 6.2 | |

TABLE 16-continued

| Comparative example | | Product name | Weight (g) | Weight ratio |
|---|---|---|---|---|
| | | Ethyl acetate | 24.8 | |
| | | Butyl acetate 98/100 | 37.2 | |
| | | Effect pigment according to example 5, NVC: 23% | 4.0 | |
| Comparative example 23 | Clearcoat | Kristalex F100 Hydrocarbon Resin, 70% by weight in butyl acetate | 5.7 | Kristalex F100 Hydrocarbon Resin:Kristalex 5140 Hydrocarbon Resin 1:4 |
| | | Kristalex 5140 Hydrocarbon Resin, 60% by weight in butyl acetate | 26.6 | |
| | | Isopropanol | 6.1 | |
| | | Ethyl acetate | 24.4 | |
| | | Butyl acetate 98/100 | 37.0 | |
| | | Effect pigment according to example 5, NVC: 23% | 4.0 | |
| Comparative example 24 | Clearcoat | Kristalex F100 Hydrocarbon Resin, 70% by weight in butyl acetate | 3.1 | Kristalex F100 Hydrocarbon Resin:Kristalex 5140 Hydrocarbon Resin 1:8 |
| | | Kristalex 5140 Hydrocarbon Resin, 60% by weight in butyl acetate | 29.6 | |
| | | Isopropanol | 6.1 | |
| | | Ethyl acetate | 24.5 | |
| | | Butyl acetate 98/100 | 36.7 | |
| | | Effect pigment according to example 5, NVC: 23% | 4.0 | |

The nail varnish compositions of comparative examples 21 to 24, after application to a synthetic fingernail and subsequent drying, showed a much poorer visual appearance than the nail varnish applications of the invention applied, which is probably attributable to the excessively low binder solids content of about 20% by weight, based on the total weight of the clearcoat. The surface-modified effect pigment was probably wetted by the solvent present in the clearcoat, and for that reason the effect pigment was unable to adopt an orientation at the surface of the clearcoat on or after application.

For production of the nail varnish compositions of comparative examples 25 to 30, the clearcoat from table 13 was added according to table 17 below to an initial charge of the respective surface-modified effect pigment according to table 17 with stirring at 600 rpm/min. The nail varnish compositions of comparative examples 25 to 30 had a binder solids content of 40% by weight, based on the total weight of the clearcoat.

TABLE 17

| Comparative example | Nail varnish composition | Weight (g) |
|---|---|---|
| 25 | Effect pigment according to comparative example 10, NVC: 59% | 2.30 |
| | Clearcoat from table 13 | 97.70 |

TABLE 17-continued

| Comparative example | Nail varnish composition | Weight (g) |
|---|---|---|
| 26 | Effect pigment according to comparative example 1, NVC: 58% | 2.40 |
| | Clearcoat from table 13 | 97.60 |
| 27 | Effect pigment according to comparative example 15, NVC: 48-52% | 2.70 |
| | Clearcoat from table 13 | 97.30 |
| 28 | Effect pigment according to comparative example 12, NVC: 10% | 13.00 |
| | Clearcoat from table 13 | 87.00 |
| 29 | Effect pigment according to comparative example 13, NVC: 10% | 13.00 |
| | Clearcoat from table 13 | 87.00 |
| 30 | Effect pigment according to comparative example 14, NVC: 10% | 13.00 |
| | Clearcoat from table 13 | 87.00 |

Table 18 summarizes the calculated compositions of the inventive examples and comparative examples that address the variation of the nail varnish parameters (always with the same effect pigment from example 5).

TABLE 18

| Sample | Kristallex F100 | Kristalex 5140 | Isopropanol | Ethyl acetate | Butyl acetate | Further solvent | Pigment acc. to example 5: | Total | Total binder content in % by weight | Total effect pigment | Total iso | Total ethyl acetate | Total butyl acetate content |
|---|---|---|---|---|---|---|---|---|---|---|---|---|---|
| Example 32 | 22.3 | 26 | 5 | 18.7 | 28 | | 4 | 104 | 30.0 | 0.88 | 6.96 | 26.02 | 67.02 |
| Example 33 | 14.8 | 34.6 | 4.5 | 19 | 27.5 | | 4 | 104.4 | 29.8 | 0.88 | 6.22 | 26.26 | 67.52 |
| Example 34 | 8.9 | 41.6 | 4.5 | 19 | 26 | | 4 | 104 | 30.0 | 0.88 | 6.26 | 26.43 | 67.31 |
| Example 35 | 4.8 | 46.3 | 4.5 | 17.9 | 26.5 | | 4 | 104 | 29.9 | 0.88 | 6.26 | 24.88 | 68.86 |

TABLE 18-continued

| Sample | Kristallex F100 | Kristalex 5140 | Isopropanol | Ethyl acetate | Butyl acetate | Further solvent | Pigment acc. to example 5: | Total | Total binder content in % by weight | Total effect pigment | Total iso | Total ethyl acetate | Total butyl acetate content |
|---|---|---|---|---|---|---|---|---|---|---|---|---|---|
| Example 36 | 27.9 | 32.5 | 3 | 11.6 | 25 | | 4 | 104 | 37.5 | 0.88 | 4.68 | 18.11 | 77.21 |
| Example 37 | 19.8 | 46.3 | 3.1 | 12.3 | 18.5 | | 4 | 104 | 40.0 | 0.88 | 5.05 | 20.02 | 74.93 |
| Example 38 | 11.8 | 55.4 | 2.9 | 11.9 | 20 | | 4 | 106 | 39.2 | 0.87 | 4.56 | 18.72 | 76.72 |
| Example 39 | 6.7 | 61.5 | 2.9 | 11.5 | 17.4 | | 4 | 104 | 40.0 | 0.88 | 4.72 | 18.70 | 76.58 |
| Example 40 | 42.9 | 50 | 0.6 | 2.6 | 3.9 | | 4 | 104 | 57.7 | 0.88 | 1.39 | 6.04 | 92.57 |
| Example 41 | 28.6 | 66.7 | 0.4 | 1.7 | 2.6 | | 4 | 104 | 57.7 | 0.88 | 0.93 | 3.95 | 95.12 |
| Example 42 | 17.1 | 80 | 0.2 | 1 | 1.7 | | 4 | 104 | 57.7 | 0.88 | 0.46 | 2.32 | 97.22 |
| Example 43 | 9.6 | 88.8 | 0.1 | 0.6 | 0.9 | | 4 | 104 | 57.7 | 0.88 | 0.23 | 1.39 | 98.38 |
| Example 44 | 22.3 | 26 | 4.7 | 19 | 28 | | 4 | 104 | 30.0 | 0.88 | 6.54 | 26.44 | 67.02 |
| Example 45 | 22.3 | 26 | 4.7 | 19 | 28 | | 4.8 | 104.8 | 29.8 | 1.05 | 6.48 | 26.21 | 67.30 |
| Example 46 | 22.3 | 26 | 4.7 | 19 | 28 | | 2 | 102 | 30.6 | 0.45 | 6.68 | 27.02 | 66.30 |
| Example 47 | 22.3 | 26 | 4.7 | 19 | 28 | | 7 | 107 | 29.2 | 1.50 | 6.34 | 25.61 | 68.05 |
| Example 48 | 22.3 | 26 | 4.7 | 19 | 28 | | 9 | 109 | 28.6 | 1.90 | 6.21 | 25.09 | 68.70 |
| Comparative example 17 | 22.25 | 26 | 14.31 | 0 | 37.44 | | 4 | 104 | 30.0 | 0.88 | 19.90 | 0.00 | 80.10 |
| Comparative example 18 | 19.13 | 19.13 | 22.33 | 39.42 | 0 | | 4 | 104.01 | 23.9 | 0.88 | 28.55 | 50.40 | 21.06 |
| Comparative example 19 | 14.87 | 23.63 | 18.5 | 32 | 0 | | 4 | 93 | 26.4 | 0.99 | 27.41 | 47.41 | 25.18 |
| Comparative example 20 | 14.9 | 34.69 | 4.6 | 15.18 | 27.5 | 3.12 (acetone) | 4 | 103.99 | 30.0 | 0.88 | 6.40 | 21.13 | 68.12 |
| Comparative example 21 | 14.3 | 16.6 | 6.3 | 25.1 | 37.9 | | 4 | 104.2 | 19.2 | 0.88 | 7.56 | 30.13 | 62.31 |
| Comparative example 22 | 9.6 | 22.2 | 6.2 | 24.8 | 37.2 | | 4 | 104 | 19.3 | 0.88 | 7.47 | 29.87 | 62.67 |
| Comparative example 23 | 5.7 | 26.6 | 6.1 | 24.4 | 37 | | 4 | 103.8 | 19.2 | 0.89 | 7.36 | 29.42 | 63.22 |
| Comparative example 24 | 3.1 | 29.6 | 6.1 | 24.5 | 36.7 | | 4 | 104 | 19.2 | 0.88 | 7.34 | 29.46 | 63.20 |

III Characterization of the Surface-Modified Effect Pigments of the Invention for Use with Preference in a Nail Varnish Composition and of the Surface-Modified Effect Pigments IIIa Measurement of Particle Size The size distribution curve of the surface-modified effect pigments of the invention that are to be used with preference in a nail varnish composition, of the surface-modified effect pigments as claimed in claim 1 and of the pigments from the comparative examples, based in each case on nonmetallic substrates in platelet form, was determined with the Malvern Mastersizer 2000 instrument according to the manufacturer's instructions. For this purpose, about 0.1 g of the respective pigment in the form of an aqueous suspension without addition of dispersing aids, with constant stirring, was introduced by means of a Pasteur pipette into the sample preparation cell of the instrument and analyzed repeatedly. The individual measurement results were used to form the averages. The scattered light signals were evaluated by the Fraunhofer method.

The size distribution curve of the surface-modified effect pigments of the invention that are to be used with preference in a nail varnish composition, of the surface-modified effect pigments as claimed in claim 1 and of the pigments from the comparative examples, based in each case on metallic substrates in platelet form, was measured with the Quantachrome Cilas 1064 instrument or the Horiba LA-930 instrument, in each case according to manufacturer's instructions. For this purpose, about 50 ml of the respective pigment were suspended in isopropanol, treated in an ultrasound bath for 300 seconds (instrument: Sonorex IK 52, from Bandelin) and then introduced by means of a Pasteur pipette into the sample preparation cell of the instrument and analyzed repeatedly. The individual measurement results were used to form the averages. The scattered light signals were evaluated by the Fraunhofer method.

In the context of this invention, average particle size $D_{50}$ is understood to mean the $D_{50}$ of the cumulative frequency distribution of the volume-averaged size distribution function as obtained by laser diffraction methods. The $D_{50}$ means that 50% of the pigments have a volume-averaged diameter less than or equal to the value specified, for example 20 μm. Correspondingly, the $D_{10}$ and $D_{90}$ values mean that, respectively, 10% and 90% of the pigments have a volume-averaged diameter equal to or less than the respective measurement.

The span $\Delta D$, defined as $$\Delta D = \frac{D_{90} - D_{10}}{D_{50}},$$

indicates the range of the particle size distribution.

With regard to the visual appearance of the surface-modified effect pigments of the invention that are to be used with preference in a nail varnish composition, or of the surface-modified effect pigments as claimed in claim 1, preference is given to a small value of $\Delta D$, i.e. a small span.

IIIb Determination of the Average Thickness of the Metallic or Nonmetallic Substrates in Platelet Form, Determination of the Average Total Thickness of the Surface-Modified Effect Pigment The average thicknesses $h_{50}$ of the surface-modified effect pigments of the invention that are to be used with preference in a nail varnish composition, the surface-modified effect pigments as claimed in claim 1 and the pigments from the comparative examples were determined by the method described in WO 2004/087816 A2 (pages 24 and 25) by means of SEM.

IIIc Determination of the Metal Oxide Content of the Synthetic Mica Platelets

The metal oxide contents of the synthetic mica platelets were determined by means of x-ray fluorescence analysis (XRF). For this purpose, the synthetic mica platelets were incorporated into a lithium tetraborate glass tablet, fixed in solid sample measurement cups and analyzed therefrom. The instrument used was the Thermo Scientific Advantix ARL instrument.

IV Optical Characterization of the Nail Varnish Compositions of the Invention

IVa Determination of Gloss (20° Geometry) and Haze

For objective determination of the visual appearance of the nail varnish compositions of the invention and of the nail varnish compositions from the comparative examples, the respective nail varnish composition was applied to glass plates in a wet film thickness of 110 μm by means of a bar applicator (Erichsen System Wasag Model 288 film applicator, from Erichsen) and then dried at room temperature. The gloss value (20° geometry) and the haze value (H log) of the nail varnish compositions thus applied were measured with the haze gloss instrument (from BYK Gardner).

For the measurement of gloss, the 20° geometry for high-gloss surfaces was employed (Byk-Gardner, digital catalog "Qualitatskontrolle fir Lacke and Kunststoffe", page 16). Both the gloss (20° geometry) and the haze (H log) were determined at least 5 different points in the nail varnish application. Table 18 below lists the averages formed therefrom for gloss (20° geometry) and haze (H log).

V Results:

Table 19 lists the gloss and haze values for selected examples and comparative examples. In addition, the pigmentation levels, the binder concentrations and the compositions of the solvents in the nail varnish compositions have been calculated.

The gloss and haze values listed in table 19 should not be considered independently of one another. Thus, a nail varnish composition having a high haze value and simultaneously a low gloss value can nevertheless have a mirror-like effect.

After application, the inventive nail varnish compositions of examples 48 to 64 showed marked leafing characteristics up to and including a mirror-like effect.

The nail varnish applications of the highest visual quality with an excellent mirror effect were obtained through the use of PVD pigments coated with phosphoric acid cetyl ester (Hostaphat CC 100) (examples 49, 51, 54, 56, 57, 58 and 59).

By contrast, the nail varnish compositions of comparative examples 27 to 30, where no additive was used, did not show any leafing effect and in some cases even showed significant formation of specks after application. The resultant gloss and haze values were accordingly poor.

In comparative example 25, the potassium salt of cetylphosphoric ester was used, which is disadvantageous.

In comparative example 26, the application contained specks. This is probably attributable to an excessively high proportion of the additive in the production of the coated metal pigment.

TABLE 19

Results of optical studies and the most important composition parameters for selected examples and comparative examples

| Example/ Comparative example | Type of effect pigment | Additive | Additive/pigment ratio in % | Pigment content [% by wt.] | Content of the preferred 3-solvent mixture*** based on the total solvent content | Content of hydrocarbon resin [% by wt.] | Gloss (20° geometry) | Haze (Hlog) |
|---|---|---|---|---|---|---|---|---|
| Example 49 | PVD* | CC 100 | 10 | 1.20 | 71.2 | 57.4 | 624.3 | 1353.9 |
| Example 50 | Pt-$** | CC 100 | 4 | 1.28 | 95.8 | 63.6 | 137.5 | 1344.9 |
| Example 51 | PVD | CC 100 | 10 | 1.33 | 95.8 | 63.6 | 358.4 | 1510.7 |
| Example 52 | PVD | Laurylphosphonic acid | 13.3 | 1.19 | 75.9 | 56.4 | 84.1 | 1289.1 |
| Example 53 | PVD | Laurylphosphonic acid | 13.3 | 1.28 | 78.7 | 59.7 | 130.7 | 1415.0 |
| Example 54 | PVD | CC 100 | 20.0 | 1.15 | 90.8 | 59.7 | 221.2 | 1450.5 |
| Example 55 | PVD | Laurylphosphonic acid | 20.0 | 1.13 | 83.3 | 61.0 | 120.2 | 1383.1 |
| Example 56 | PVD | CC 100 | 10.0 | 1.24 | 84.8 | 61.2 | 149.6 | 1390.4 |
| Example 57 | PVD | CC 100 | 20.0 | 1.14 | 88.5 | 58.4 | 240.1 | 1568.0 |
| Example 58 | PVD | CC 100 | 40.0 | 0.98 | 88.4 | 58.5 | 455.8 | 1496.1 |
| Example 59 | PVD | CC 100 | 10.0 | 1.25 | 88.4 | 58.5 | 176.6 | 1499.3 |
| Example 60 | Pt-$ | CC 100 | 5.0 | 1.31 | 95.1 | 62.1 | 101.0 | 1290.0 |
| Example 61 | Pt-$ | CC 100 | 20.0 | 1.13 | 100.0 | 64.4 | 107.0 | 1317.7 |
| Example 62 | Pt-$ | CS 100 | 5.0 | 1.29 | 100.0 | 64.6 | 125.1 | 1366.0 |
| Example 63 | Pt-$ | CC 100 | 2.5 | 1.33 | 100.0 | 64.5 | 121.1 | 1347.6 |
| Example 64 | Pt-$ | CC 100 | 7.5 | 1.27 | 100.0 | 64.3 | 99.9 | 1289.0 |
| Comparative example 28 | PVD | — | 0 | 1.30 | 100.0 | 36.2 | 101.8 | 121.6 |
| Comparative example 29 | PVD | — | 0 | 1.30 | 100.0 | 36.2 | 19.2 | 565.6 |
| Comparative example 30 | PVD | — | 0 | 1.30 | 100.0 | 36.2 | 100.4 | 134.5 |
| Comparative example 27 | Pt-$ | — | 0 | 1.35 | 96.1 | 40.5 | 104.4 | 175.5 |

TABLE 19-continued

Results of optical studies and the most important composition parameters for selected examples and comparative examples

| Example/ Comparative example | Type of effect pigment | Additive | Additive/pigment ratio in % | Pigment content [% by wt.] | Content of the preferred 3-solvent mixture*** based on the total solvent content | Content of hydrocarbon resin [% by wt.] | Gloss (20° geometry) | Haze (Hlog) |
|---|---|---|---|---|---|---|---|---|
| Comparative example 25 | Pt-$ | Hostaphat CK 100 | 20 | 1.13 | 100.0 | 64.6 | 73.2 | 1154.9 |
| Comparative example 26 | Pt-$ | CS 120 | 20 | 1.16 | 100.0 | 64.5 | 125.2 | 1363.5 |

*All PVD pigments are abbreviated here merely to "PVD"; the further details can be found in the corresponding tables above.
**"Pt-$" refers in this table to all wet-ground pigments having an average thickness below 100 nm. Further details can be found in the corresponding tables above.
***Mixture of ethyl acetate, butyl acetate and isopropanol.

The invention claimed is:

1. A nail varnish composition comprising:
   a) at least one effect pigment surface-modified with a starting material (additive), wherein the effect pigment comprises a PVD aluminum pigment in platelet form and optionally comprises at least one coating applied to the PVD aluminum pigment, the PVD aluminum pigment having an average thickness $h_{50}$ ranging from 13 nm to 60 nm, and wherein the starting material (additive) used for surface modification of the PVD aluminum pigment or the coating comprises phosphoric acid cetyl ester in an amount ranging from 10% by weight to 50% by weight based on the total weight of the optionally coated PVD aluminum pigment;
   b) at least one hydrocarbon resin as binder; and
   c) at least one non-aqueous solvent.

2. The nail varnish composition as claimed in claim 1, wherein the hydrocarbon resin comprises 80% to 100% by weight of the total weight of binder comprised in the nail varnish composition.

3. The nail varnish compositions as claimed in claim 1, wherein the hydrocarbon resin comprises at least two different hydrocarbon resins having an average molecular weight MW of 1200 to 1600 and an average molecular weight MW of 4500 to 5500 in a weight ratio of 1:1 to 1:10.

4. The nail varnish compositions as claimed in claim 1, wherein the content of hydrocarbon resin is within a range from 25% by weight to 64% by weight, based on the total weight of the nail varnish composition.

5. The nail varnish composition as claimed in claim 1, comprising the non-aqueous solvent mixture, the non-aqueous solvent mixture comprising isopropanol, ethyl acetate and butyl acetate.

6. The nail varnish composition as claimed in claim 5, wherein the non-aqueous solvent mixture of isopropanol, ethyl acetate and butyl acetate comprises 70% to 100% by weight of the total weight of solvent comprised in the nail varnish composition.

7. The nail varnish composition as claimed in claim 5, wherein the proportion of isopropanol is below 20% by weight, based on the total weight of solvent comprised in the nail varnish composition.

8. The nail varnish composition as claimed in claim 1, additionally comprising at least one of a plasticizer, antioxidant, antisettling agent, preservative, oil, wax, free-radical scavenger, wetting additive, dispersing aid, wetting agent, antifoam, perfume, neutralizing agent, thickener, UV blocker, humectant, vitamin, protein, and combinations thereof.

9. The nail varnish composition as claimed in claim 1, wherein the nail varnish composition after application to a glass plate by means of a bar applicator in a wet film thickness of 100 μm and subsequent drying at room temperature has at least 150 gloss units, measured at 20° geometry, and at least 1200 haze units (Hlog).

10. A nail varnish composition comprising
    a) at least one effect pigment surface-modified with a starting material (additive), wherein the effect pigment comprises a PVD aluminum pigment and optionally comprises at least one coating applied to the PVD aluminum pigment,
    b) at least one hydrocarbon resin as binder and
    c) at least one non-aqueous solvent or non-aqueous solvent mixture,
    wherein one or more of the coating and the starting material (additive) used for surface modification of the effect pigment comprises phosphoric acid cetyl ester.

11. The nail varnish composition as claimed in claim 10, wherein the hydrocarbon resin comprises 80% to 100% by weight of the total weight of binder comprised in the nail varnish composition.

12. The nail varnish compositions as claimed in claim 10, wherein the hydrocarbon resin comprises at least two different hydrocarbon resins having an average molecular weight MW of 1200 to 1600 and an average molecular weight MW of 4500 to 5500 in a weight ratio of 1:1 to 1:10.

13. The nail varnish compositions as claimed in claim 10, wherein the content of hydrocarbon resin is within a range from 25% by weight to 64% by weight, based on the total weight of the nail varnish composition.

14. The nail varnish composition as claimed in claim 10, comprising the non-aqueous solvent mixture, the non-aqueous solvent mixture comprising isopropanol, ethyl acetate and butyl acetate.

15. The nail varnish composition as claimed in claim 14, wherein the non-aqueous solvent mixture of isopropanol, ethyl acetate and butyl acetate comprises 70% to 100% by weight of the total weight of solvent comprised in the nail varnish composition.

16. The nail varnish composition as claimed in claim 14, wherein the proportion of isopropanol is below 20% by weight, based on the total weight of solvent comprised in the nail varnish composition.

17. The nail varnish composition as claimed in claim 10, additionally comprising at least one of a plasticizer, antioxidant, antisettling agent, preservative, oil, wax, free-radical scavenger, wetting additive, dispersing aid, wetting agent, antifoam, perfume, neutralizing agent, thickener, UV blocker, humectant, vitamin, protein, and combinations thereof.

18. The nail varnish composition as claimed in claim 10, wherein the nail varnish composition after application to a glass plate by means of a bar applicator in a wet film thickness of 100 μm and subsequent drying at room temperature has at least 150 gloss units, measured at 20° geometry, and at least 1200 haze units (Hlog).

* * * * *